United States Patent
Simon et al.

(10) Patent No.: US 6,204,067 B1
(45) Date of Patent: Mar. 20, 2001

(54) METHODS OF IDENTIFYING MODULATORS OF THE ESTROGEN RECEPTOR

(75) Inventors: Sanford M. Simon, New York, NY (US); Melvin S. Schindler, Okemos, MI (US); Yu Chen, New York, NY (US)

(73) Assignee: Board of Trustees Operating Michigan State University, East Lansing, MI (US)

( * ) Notice: Subject to any disclaimer, the term of this patent is extended or adjusted under 35 U.S.C. 154(b) by 0 days.

(21) Appl. No.: 09/335,457

(22) Filed: Jun. 17, 1999

(51) Int. Cl.[7] .......................... G01N 31/22; G01N 21/80; G01N 33/48; C07C 211/04
(52) U.S. Cl. ..................... 436/163; 436/172; 436/63; 436/111; 564/324
(58) Field of Search ................ 564/324; 436/163, 436/172, 63, 111; 435/7.8

(56) References Cited

U.S. PATENT DOCUMENTS 5,851,789  12/1998  Simon et al. .................... 435/32

OTHER PUBLICATIONS

Altan et al., *J.Exp.Med.* 187: 1583–1598 (1998) No Month.
Altan et al., *Proc Natl Acad Sci U. S. A.* 96:4432–4437 (Apr. 1999).
Berman et al., *Leukemia* 9:1631–37 (1995) No Month.
Berman et al., *Blood* 77:818–25 (Feb. 1991).
Callaghan et al. *Br.J.Cancer* 71:294–299 (1995) No Month.
Chatterjee et al., *British Journal of Cancer* 62:712–717 (1990) No Month.
Cole et al., *Science*, 258:1650–1654 (Dec. 1992).
Ehring et al., *J.Gen.Physiol.* 104:1129–1161 (1994) No Month.
Fisher et al., *J.Natl.Canc.Inst.* 90:1371–1388 (Sep. 1998).
Garlid et al., *J.Biol.Chem.* 258:7974–7980 (Jul. 1983).
Gekle et al., *American Journal Of Physiology* 268:F899–F906 (1995) No Month.
Goulian et al., *Biophys.J.* 74:328–337 (Jan. 1998).
Greenberg et al., *Cancer Res.* 47: 70–74 (1987).
Gruner et al., *Ann.N.Y.Acad.Sci.* 625:685–697 (1991) No Month.
Higgins et al., *TIBS*, 17:18–21 (Jan. 1992).
Hurwitz et al., *Blood* 89:3745–3754 (May 1997).
Jaiyesimi et al., *Journal of Clinical Oncology* 13:513–529 (Feb. 1995).
Jordan, *Proceedings of the Society for Experimental Biology & Medicine* 208:144–149 (1995) No Month.
Love et al., *N.Engl.J.Med.* 326:852–856 (Mar. 1992).
Ma, L et al., *Biochem Biophys. Res. Commun.,* 182:675–681 (Jan. 1992).
Rostovtseva et al., *Biophys.J.* 75:1783–1792 (Oct. 1998).
Sato et al.,*Journal of Experimental Medicine* 123:185–190 (1977) No Month.
Schindler et al.,*Biochemistry* 35:2811–2817 (Mar. 1996).
Seelig et al., *Biochim.Biophys.Acta* 939:267–276 (1988) No Month.
Song et al., *Journal of Pharmacology & Experimental Therapeutics* 277: 1444–1453 (1996).
Sun et al., *J.Biol.Chem.* 267:19147–19154 (Sep. 1992).
Sundquist et al., *Biochemical & Biophysical Research Communications* 168:309–313 (Apr. 1990).
Tartakoff, *Cell* 32:1026–1028 (1983) No Month.
Turner et al., *Endocrinology* 122:1146–1150 (1988) No Month.
van Weert et al., *J. Cell Biol.* 130:821–834 (1995) No Month.
Weinlander et al., *Journal of Cancer Research & Clinical Oncology* 123:452–455 (1997) No Month.
Williams et al., *Journal of Cellular Biochemistry* 66:358–369 (1997) No Month.
Wiiliams et al.,*J.Biol.Chem.* 271:12488–12495 (May 1996).
Wiseman et al., *FEBS Letters* 330:53–56 (Sep. 1993).
Wiseman, *Trends in Pharmacological Sciences* 15:83–89 (Mar. 1994).
Zhang et al., *Journal of Clinical Investigation* 94:1690–1697 (Oct. 1994).

*Primary Examiner*—Ardin H. Marschel
*Assistant Examiner*—Marjorie A. Moran
(74) *Attorney, Agent, or Firm*—Klauber & Jackson

(57) ABSTRACT

The present invention discloses the mechanism of tamoxifen mediated inhibition of acidification. This mechanism information is then used to design methods of identifying compounds that will have the pharmaceutical effect of tamoxifen without the corresponding side-effects.

26 Claims, 12 Drawing Sheets

−o− No Octanol
−●− 11000 Octanol
−*− 1100 Octanol

METHODS OF IDENTIFYING MODULATORS OF THE ESTROGEN RECEPTOR

GOVERNMENTAL SUPPORT

The research leading to the present invention was supported, at least in part, by a grant from NIH MSTP GM07739 and ACS grant RPG-98-177-01-CDD. Accordingly, the Government may have certain rights in the invention.

FIELD OF THE INVENTION

The present invention pertains to ways of identifying compounds that can modulate the estrogen receptor without having the undesirable side-effects of pharmaceuticals such as tamoxifen.

BACKGROUND OF THE INVENTION

Tamoxifen is the most commonly used treatment for breast cancer [Jaiyesimi et al., *Journal of Clinical Oncology* 13:513–529 (1995)]. In addition, it is currently being considered for widespread use in healthy women for breast cancer prevention [Jordan, *Proceedings of the Society for Experimental Biology & Medicine* 208:144–149 (1995); Fisher et al., *J.Natl.Canc.Inst.* 90:1371–1388 (1998)]. Yet, despite its widespread use, its mechanisms of action remain obscure. Tamoxifen is a known estrogen receptor modulator that acts as an antagonist or partial-agonist. But it has also been reported to have many pleiotropic effects both in vivo and in vitro that cannot be explained by an interaction with the estrogen receptor [Kellen, *Tamoxifen: Beyond the Antiestrogen*, Birkhäuser, Boston (1996)]. For example, tamoxifen has been shown to enhance drug sensitivity of multidrug resistant cells [Chatterjee and Harris, *British Journal of Cancer* 62:712–717 (1990); Berman et al., *Blood* 77:818–825 (1991); Berman et al., *Leukemia* 9:1631–1637 (1995); Weinlander et al., *Journal of Cancer Research & Clinical Oncology* 123:452–455 (1997); Altan et al., *J.Exp.Med.* 187: 1583–1598 (1998)], inhibit bone resorption and osteoporosis both in vivo and in vitro [Love et al., *N.Engl.J.Med.* 326:852–856 (1992)] and inhibit a number of channels, including the volume activated chloride channel [Zhang et al., *Journal of Clinical Investigation* 94:1690–1697 (1994); Ehring et al., *J.Gen.Physiol.* 104:1129–1161 (1994)] and calcium channels[Greenberg et al., *Cancer Res.* 47: 70–74 (1987); Song et al., *Journal of Pharmacology & Experimental Therapeutics* 277: 1444–1453 (1996); Williams et al., *J.Biol.Chem.* 271:12488–12495 (1996); Turner et al., *Endocrinology* 122:1146–1150 (1988)]. These effects have been attributed to inibition of P-glycoprotein [Callaghan and Higgins *Br.J-.Cancer* 71:294–299 (1995)], calmodulin [Williams et al., *J.Biol.Chem.* 271:12488–12495 (1996)], and direct channel interaction [Zhang et al., *Journal of Clinical Investigation* 94:1690–1697 (1994)] respectively. Thus, the administration of tamoxifen as an estrogen receptor modulator results in a number of undesirable side-effects which are totally independent of the modulation of the estrogen receptor.

As mentioned above, tamoxifen has been shown to enhance drug sensitivity of multidrug resistant cells. Different drug-resistant cells overexpress a variety of membrane proteins including a subunit of a vacuolar $H^+$-ATPase [Ma, L et al., *Biochem Biophys. Res. Commun.*, 182:675–681 (1992)], a protein with homology to CFTR [Cole et al., *Science*, 258:1650–1654 (1992)] and the P-glycoprotein, a 170–180 kD plasma membrane glycoprotein [Gottesman et al., *Annu. Rev. Biochem.*, 62:385–427 (1993)]. The most generally accepted hypothesis for MDR suggests the P-glycoprotein uses ATP to power a molecular pump that removes chemotherapeutic molecules from the cell [Dano et al., *Biochem Biophys.*, 323:466–483 (1973) and reviewed in Gottesman et al., *Annu. Rev. Biochen.*, 62:385–427 (1993)]. This model proposes that chemotherapeutic agents diffuse down a concentration gradient into the cell and that the pump either transports the drugs out of the cytosol or serves as a flippase to expel them from the bilayer [Higgins et al., *TIBS*, 17:18–21 (1992)]. More recently it has been shown that changes of organelle pH associated with multidrug resistance (MDR) in tumor cells can lead to multi-drug resistance [see U.S. Pat. No. 5,851,789, Issued on Dec. 22, 1998, and U.S. application Ser. No. 09/080,739, filed May 18, 1998, the disclosures of which are each hereby incorporated by reference herein in their entireties] and that the effect of tamoxifen on MDR is related to the de-acidification of the cellular organelles.

Therefore, there is a need to identify modulators of the estrogen receptor that do not result in the same side-effects as tamoxifen. Thus, there is a need to determine the effects of tamoxifen that are independent of its role in modulation of the estrogen receptor. Furthermore, there is a need to identify the role tamoxifen plays in causing these effects. Finally, there is a need to identify assays for screening potential estrogen receptor modulators that can modulate the estrogen receptor as tamoxifen does, but do not cause the other undesirable effects.

The citation of any reference herein should not be construed as an admission that such reference is available as "Prior Art" to the instant application.

SUMMARY OF THE INVENTION

The present invention provides methods of selecting compounds/agents that have the positive pharmaceutical effects of tamoxifen, without the undesirable side-effects. These compounds can be known analogs of estrogen and/or effectors (e.g., agonists or antagonists) of the estrogen receptor, or alternatively, the compounds can be tested for estrogen receptor binding activity prior to/or after performing the methods disclosed herein.

Therefore the present invention provides a method of selecting a modulating agent of the estrogen receptor that does not dissipate a transmembrane pH gradient to the extent that tamoxifen does. One such embodiment comprises contacting an agent with a vesicle that is surrounded by a membrane under conditions in which tamoxifen dissipates a transmembrane pH gradient and then determining the level (e.g., magnitude) of the transmembrane pH gradient. In this case, the transmembrane pH gradient forms because the pH inside of the membrane differs from that outside of the membrane.

In a preferred embodiment the agent has previously been shown to be able to modulate the estrogen receptor. A modulating agent that does not dissipate the transmembrane pH gradient to the extent that tamoxifen does is identified and/or selected. In a preferred embodiment the modulating agent that is selected does not measurably (and/or significantly) dissipate the transmembrane pH gradient.

An alternative embodiment further provides the step of determining the level (e.g., magnitude) of surface charge on the membrane. A modulating agent is then selected when it neither dissipates a transmembrane pH gradient to the extent that tamoxifen does, nor alters the surface charge on the membrane to the extent that tamoxifen does. Preferably, the modulating agent neither measurably (and/or significantly) dissipates a transmembrane pH gradient nor measurably (and/or significantly) alters the surface charge on the membrane.

The determination of the level of the transmembrane pH gradient can be performed using a number of different methods including directly with an electrode or a calibratable pH indicator or pH sensitive probe. In one particular embodiment, the level of the transmembrane pH gradient is performed with a fluorescent probe. In an embodiment exemplified below the fluorescent probe is acridine orange.

In one embodiment, the vesicle is a mammalian cell. In a particular embodiment of this type the mammalian cell is a human cell. In another embodiment, the vesicle is a organelle. In one such embodiment the organelle is a mammalian organelle. In a particular embodiment of this type the organelle is a secretory compartment. In a particular embodiment exemplified below, the mammalian organelle is a recycling endosome. In one such method, determing the level of the transmembrane pH gradient is performed with fluorescent-labeled transferrin.

In another embodiment the vesicle is a yeast vacuole. In still another embodiment the vesicle is an inverted bacterial membrane vesicle. In yet another embodiment the vesicle is a liposome. In one such method, determining the level of the transmembrane pH gradient is performed using pyranine as a fluorescent probe.

The present invention also provides a method of selecting a modulating agent of the estrogen receptor that does not modify the surface charge on a membrane to the extent that tamoxifen does. One such embodiment comprises contacting an agent with a vesicle surrounded by a membrane under conditions in which tamoxifen changes the surface charge on a membrane and determining the level (e.g., magnitude) of surface charge on the membrane. In a preferred embodiment the agent has previously been shown to be able to modulate the estrogen receptor. A modulating agent is selected that does not alter the surface charge on the membrane to the extent that tamoxifen does. Preferably the modulating agent selected does not measurably (and/or significantly) alter the surface charge on the membrane.

Again many types of vesicles can be used. In one such embodiment the vesicle is a mammalian cell. In a particular embodiment of this type the mammalian cell is a human cell. In another embodiment, the vesicle is a organelle. In one such embodiment the organelle is a mammalian organelle. In a particular embodiment of this type the organelle is a secretory compartment. In another embodiment the vesicle is a yeast vacuole. In still another embodiment the vesicle is an inverted bacterial membrane vesicle. In yet another embodiment the vesicle is a liposome.

Once a modulating agent is identified/selected by an in vitro or in situ assay, the modulating agent can be tested in an animal model in vivo and then can be tested in clinical studies. For example, protocols such as have already been performed for estrogen receptor modulators, including tamoxifen, can be carried out to select a suitable drug.

Indeed, the present invention further provides pharmaceutical compositions comprising the modulating agents obtained by the methods of the present invention. Preferably the pharmaceutical compositions further comprise a pharmaceutical carrier.

These and other aspects of the present invention will be better appreciated by reference to the following drawings and Detailed Description.

BRIEF DESCRIPTION OF THE DRAWINGS

FIG. 1A is the pre-incubation with tamoxifen. Acridine orange is a weak base that accumulates to self-quenching concentrations into acidic compartments. Thus, the presence of acidic compartments decreases the total fluorescence by decreasing the concentration of free AO outside those compartments. Microsomes were suspended in acridine orange (AO) and, after establishing the baseline, 1 mM Tris-ATP was added to begin acidification (at 300 seconds). This caused a slow decrease of total fluorescence over 1200 seconds (Ctrl). Addition of the protonophore nigericin (5 $\mu$M Nig) at t=1500 returned the fluorescence levels demonstrating the fluorescence decrease was the consequence of acidification. This inhibitory effect of tamoxifen (Tam) on acidification was apparent at 1 $\mu$M and increased in a dose-dependent maner (2 $\mu$M; 4 $\mu$M; 8 $\mu$M). Pre-treatment of microsomes with 10 nM bafilomycin $A_1$(Baf) also blocked acidification. The Inset of FIG. 1A shows the Dose-response of tamoxifen on acidification; the Acidification was assayed as in FIG. 1A. FIG. 1B shows the effect of tamoxifen added during the acidification: Ten minutes after the addition of 1 mM Tris-ATP, 8 $\mu$M tamoxifen or 100 nM bafilomycin $A_1$ was added which rapidly reversed acidification of the organelles. In the absence of tamoxifen or bafilomycin $A_1$, the organelles continued to acidify. Ten minutes later 5 $\mu$M nigericin was added. FIG. 1C shows the results of the acidification in recycling endosomes assayed by FITC-transferrin. Cells were incubated with FITC-transferrin, which is endocytosed and localized within the endosoies. After lysing the cells a microsornal fraction was harvested. The fluorescence emission at 520 nm was monitored in response to excitation at 488 and 450 nm and the ratio was plotted. When excited at 488 nm, the fluorescence of FITC increases with increasing pH but when excited at 450 nm, the fluorescence of FITC is pH independent. Therefore, a decreasing ratio indicates acidification. Upon addition of ATP (t=1080 seconds) there was acidification of the lumen of the microsomes as assayed by a decrease in the ratio of the 488:450 nm emission. Nigericin was added (t=2500 sec) to confirm that the fluorescent shift was the result of acidification. Successive additions of 2.5 $\mu$M tamoxifen caused alkalinization of endosomes. Nigericin was added at the end to equilibrate the pH.

FIG. 2A shows the effect of tamoxifen, ammonium sulfate, and chloride on yeast vacuole acidification. Vacuoles were suspended in buffer (KCl except K-glutamate labeled) containing AO in the presence of tamoxifen (2 $\mu$M or 8 $\mu$M Tam), ammonium sulfate (1 mM $NH4^+$) or K-glutamate instead of KCl. ATP (1.5 mM) was added at 50 sec to initiate acidification and nigericin (1 $\mu$M Nig) was added at 400 sec. The presence of tamoxifen caused a dose dependent inhibition of acidification. Ammonium sulfate, at much higher concentrations, also caused a slight inhibition. When glutamate was used instead of chloride, acidification decreased, consistent with a chloride channel dissipating the $V_m$. FIG. 2B shows the effect of adding tamoxifen or ammonium sulfate during acidification of yeast vacuoles. Vacuoles were in a KCl buffer containing AO, and acidification was initiated by addition of ATP (1.5 nM) at 50 sec. At 250 sec, either ammonium sulfate (1 mM) or tamoxifen (2 $\mu$M) was added. Each caused a step increase in AO fluorescence, indicating alkalinization. Subsequently, AO fluorescence continued to increase when tamoxifen was added but slowly decreased when amnonium sulfate was added.

FIG. 3A shows the effect of tamoxifen and chloride on $V_m$ of yeast vacuoles. Vacuoles were suspended in KCl or K-gluconate buffer with 1 μM Oxonol V. Oxonol V is a mebrane permeable, anionic dye. Thus, it accumulates into vesicles of positive $V_m$, resulting in fluorescence quenching. Addition of ATP resulted in a vATPase generated inside-positive $V_m$ of the vacuoles, and quenching of Oxonol V fluorescence. In the absence of tamoxifen, the $V_m$ was greater in K-gluconate than KCl, consistent with a chloride channel dissipating the $V_m$. The presence of tamoxifen decreased the ATP generated $V_m$ in both KCl and K-gluconate to similar levels. FIG. 3B shows the effect of tamoxifen and chloride on bafilomycin inhibitable ATPase activity of yeast vacuoles. ATPase levels were quantified by measuring released phosphate as described in materials and methods (see Example 1, below). Samples were split in two and processed±bafilomycin $A_1$ to determine vATPase activity. In the absence of tamoxifen, ATPase activity was greater in chloride than gluconate. This is because in the absence of chloride, there is a large $V_m$ against the vATPase. Tamoxifen increased the ATPase activity in both buffers.

FIG. 6A shows that the pH shift caused a rapid alkaline shift of the lumen in the presence of tamoxifen. This cannot be due to lysis because there was no decrease of total fluorescence indicating lack of dye leakage into DPX containing external buffer. Ammonium, at 2000× concentration, caused a similar alkaline jump. But the rate of pH dissipation was faster after the alkaline jump with tamoxifen than ammonium. FIG. 6B shows that FCCP and valinomycin each increased the rate of pH dissipation, but did not cause an alkaline jump upon pH change.

FIG. 7A shows the effect on liposome pH by weak base addition. Pyranine loaded liposomes with $pH_{in}$= 6.3 was diluted into KCl buffer of same pH and 10 mM DPX. Pyranine loaded liposomes with $pH_{in}$=6.3 were diluted into buffer with $pH_{out}$=6.3. At 50 sec, tamoxifen (2 μM, or 8 μM) or NH$_4$Cl (5 mM) was added. At 700 sec, nigericin (1 μM) was added. Addition of tamoxifen or NH$_4$Cl resulted in alkalinization of the lumen, presumably due to selective influx and protonation of the uncharged species. Importantly, following the alkaline jump, the pH re-equilibrated much faster when tamoxifen was used, suggesting tamoxifen mediated proton permeability. FIG. 7B shows the octanol partitioning of tamoxifen. Tamoxifen (20 μM) in PBS was mixed with 1:1000 or 1:100 volume of octanol as indicated. The tamoxifen concentration of the aqueous phase was determined using absorbance spectroscopy. Notice 1:1000 volume octanol was able to extract approximately ~50% tamoxifen from the aqueous phase. This indicates that tamoxifen partitions three orders of magnitude into the lipid phase and is consistent with the greater potency of tamoxifen as compared to ammonium in FIG. 7A.

FIG. 8A shows increasing concentrations of tamoxifen caused a dose dependent increase of pH equilibration. The weak base NH$_4$Cl, at 10×concentration used to observe a significant weak base effect (see FIG. 6), had no effect. FIG. 8B shows that FCCP and valinomycin each increased the rate of pH dissipation. Tamoxifen increased the rate faster than saturating concentrations of FCCP. Tamoxifen and valinomycin together were additive and not synergistic. These two observations suggest that tamoxifen cannot be a pure protonophore, but must mediate an electroneutral process.

FIG. 9A shows the rate of chloride influx into liposomes. Lucigenin, a non-permeable fluorescent probe that is collisionally quenched by chloride, was used to assay liposome chloride concentration. Lucigenin loaded liposomes made with an internal solution of 150 mM KNO$_3$, were diluted into 150 mM KNO$_3$ buffer and one of the follow compounds: carrier, tamoxifen (2 μM, 4 μM, 8 μM), valinomycin (1 μM), or both tamoxifen (4 μM) and valinomycin (1 μM). At 50 sec, 50 mM KCl was added and the internal chloride concentration was followed using lucigenin fluorescence. Tamoxifen caused a dose dependent influx in chloride. Valinomycin also increased chloride influx by dissipating $V_m$. Importantly, tamoxifen and valinomycin together were additive, implying that tamoxifen is not a pure chloride ionophore but mediates electroneutral chloride influx. FIG. 9B shows the effect of chloride on tamoxifen mediated proton permeability. Pyranine loaded liposomes made with internal solution of 300 mM K-glutamate, pH 8.1 was diluted into the same external solution in the presence or absence tamoxifen and 50 mM KCl as denoted in legend. At 50 sec, $pH_{out}$ was shifted to pH 6.9 and $pH_{in}$ was followed. In the absence of chloride, tamoxifen had no effect on the rate of pH equilibration. The presence of chloride reconstituted the effect of tamoxifen seen in FIG. 8. FIG. 9C shows the results with liposomes made as in FIG. 9B were diluted into 300 mM K-glutamate solution. Addition of 4 μM tamoxifen caused an alkaline shift similar to FIG. 7A. But the rate of re-equilibration was much slower than in FIG. 7A. Addition of two aliquots of 50 mM KCl caused increasing rate of acidification, presumably due to Cl⁻/H⁺ co-influx.

DETAILED DESCRIPTION OF THE INVENTION

Figure 1A:
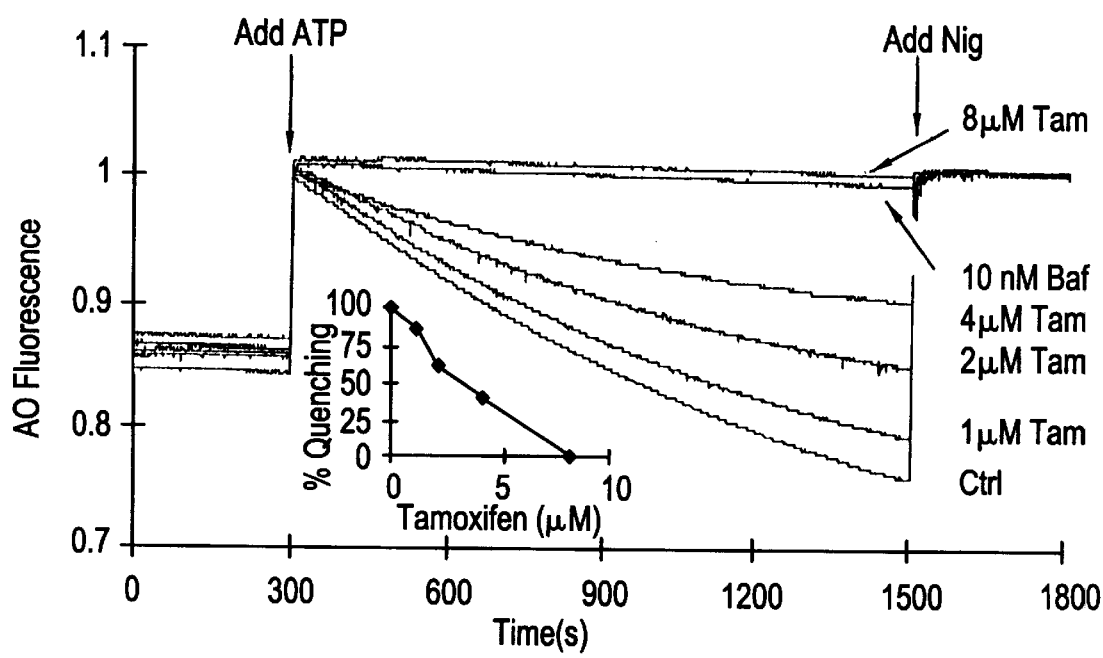
FIGS. 1A–1C show the effect of tamoxifen on in vitro acidification of MCF-7/ADR organelles.

The present invention provides methods of identifying compounds that will have the pharmaceutical effect of tamoxifen without the corresponding adverse side-effects. Tamoxifen has been reported to inhibit acidification of cytoplasmic organelles in mammalian cells. As disclosed herein the mechanism of this inhibition is investigated using in vitro assays on isolated organelles and liposomes. Tamoxifen is shown to inhibit ATP dependent acidification in organelles from a variety of sources, including isolated microsomes from mammalian cells, vacuoles from *S. cerevisiae*, and inverted membrane vesicles from *E. coli*. Tamoxifen increased the ATPase activity of the vacuolar proton ATPase, but decreased the membrane potential ($V_m$) generated by this proton pump, indicating that tamoxifen may act by increasing proton permeability. In liposomes, tamoxifen increased the rate of pH dissipation. Studies comparing the effect of tamoxifen on pH gradients using different salt conditions and with other known ionophores indicate that tamoxifen affects transmembrane pH through two independent mechanisms. First, as a lipophilic weak base it partitions into acidic vesicles, resulting in rapid neutralization. Second, it mediates coupled, electroneutral transport of proton or hydroxide with chloride. Through providing the biochemical mechanism(s) for the effects of tamoxifen that are independent of the estrogen receptor, the present invention allows the prediction of side-effects due to tamoxifen. Moreover, as provided herein, this information allows the design of drug screens to select for estrogen-receptor antagonists without these side-effects.

In addition, tamoxifen effects the surface charge of biological membranes. The surface of biological membranes are covered with charges. The charges come from a variety of sources including the acidic head groups on the phospholipids, charges on membrane proteins, charges on the sugar groups that modify some proteins and lipids, and from various molecules that are absorbed onto the membrane. These charges directly effect the electric field across the biological membrane. Thus, they affect the activity of many of the membrane-embedded proteins and their signaling events. Numerous local anaesthetics work by absorbing to the lipid bilayer and changing the surface charge on the bilayer and thus affecting the activity of the various proteins required for neuronal activity. Tamoxifen, therefore appears to act in a similar fashion.

Thus, the present invention demonstrates that many of the effects of tamoxifen on cells can be attributed to either membrane active effects on organelle acidification or surface charge. Tamoxifen affects the pH gradients both by acting as a weak base and by acting as a proton-chloride co-transporter. Tamoxifen, also absorbs to the bilayer at high concentrations and since it is partially charged in physiological solutions, this will substantially increase the number of charges on the surface of the membrane. This, in turn, accounts for many of the effects of tamoxifen on membrane proteins including ion channels, pumps and receptors. Each of these effects are independent of the estrogen receptor. Therefore the present invention provides screens for other estrogen-receptor antagonists that do not also affect organellar acidification and therefore will not share the same physiological effects as tamoxifen.

Therefore, if appearing herein, the following terms shall have the definitions set out below:

As used herein a "vesicle" is a self-contained particle, generally spherical in shape, having an aqueous interior surrounded by an outer membrane that separates that internal aqueous material from the outside environment, (the outside environment is generally an aqueous medium). Preferably the outer membrane contains one or more lipids. Examples of vesicles of the present invention include but are not limited to an intact cell, an organelle such as the recycling endosomes, a yeast vacuole, an inverted bacterial membrane vesicle, and a liposome.

As used herein a "secretory compartment" is an intracellular vesicular compartment e.g., an organelle, that is involved in the export of chemical substances including biomolecules such as lipids and proteins from the cell. Examples of secretory compartments include the perinuclear recycling compartment (PRC), the recycling endosomes, the secretory vesicles, and the trans-Golgi network (TGN).

As used herein, a "measure of the pH" of a vesicle can be any determination that can be correlated to the pH of the vesicle. Such means include measuring the pH directly, or indirectly as further exemplified below. The pH of a vesicle including an intracellular vesicular compartment can be directly determined with an electrode or a calibratable pH indicator or pH sensitive probe. Alternatively the minimum (or maximum) pH can be determined, e.g. using a pH indicator or pH sensitive probe that has an altered property (such as fluorescence or color) below (or above) a particular pH. Such measurements can be made with respect to the transmembrane pH gradient of a vesicle.

Examples of direct pH sensitive probes include acridine orange (as exemplified below) and Lysosensor Blue DND-167 which can be used for determining the pH of the intracellular vesicular compartments, for example. pH sensitive probes can also be targeted to specified intracellular vesicular compartments. For example, a pH-sensitive probe can be targeted via specific receptors to the endosomes, e.g., using the transferrin receptor (as exemplified below), or to the Golgi, using particular toxins such as verotoxin. Acridine orange emission in the red can be an assay for formation of a pH gradient across intracellular membranes. Lysosensor Blue DND-167 only emits fluorescence below pH 5.8 and its emission is diagnostic of formation of a pH gradient across the intracellular membranes.

As used herein a modulating agent of the estrogen receptor that "does not dissipate a transmembrane pH gradient to the extent that tamoxifen does" is an agent that dissipates a transmembrane pH gradient measurably less than tamoxifen when tested at equal concentrations. Preferably at comparable pharmaceutically relevant concentrations, tamoxifen causes a 50% greater dissipation, more preferably tamoxifen causes a 90% greater dissipation, and most preferably, the agent does not measurably (and/or significantly) dissipate the transmembrane pH gradient whereas tamoxifen does.

As used herein a modulating agent of the estrogen receptor that "does not modify the surface charge on a membrane to the extent that tamoxifen does" is an agent that modifies the surface charge on a membrane measurably less than tamoxifen when tested at equal concentrations. Preferably at comparable pharmaceutically relevant concentrations, tamoxifen causes a 50% greater modification, more preferably tamoxifen causes a 90% greater modification, and most preferably, the agent does not measurably (and/or significantly) modify the surface charge on a membrane whereas tamoxifen does.

Drug Assays and Screens

A potential drug, e.g., a modulating agent, can be obtained by a number of means including from a commercially available chemical library such as is available from most large chemical companies including Merck, Glaxo Welcome, Bristol Meyers. Squib, Monsanto/Searle, Eli Lilly, Novartis, and Pharmacia UpJohn. More particularly, there are presently a vast number of potential estrogen receptor modulators that have been described, including those compiled in U.S. Pat. No. 5,889,042 Issued Mar. 30, 1999; U.S. Pat. No. 5,866,560, Issued Feb. 2, 1999; and U.S. Pat. No. 5,880,137 Issued, Mar. 9, 1999, the disclosures of which are each hereby incorporated herein by reference in their entireties. Indeed small structural changes in the structure of estrogen agonists have been found to cause profound differences in biological properties. Droloxifene (3-hydroxytamoxifen) for example, has a 10–60-fold higher binding affinity to the estrogen receptor relative to tamoxifen, indicating the value of testing such compounds by the methods disclosed within.

Alternatively, potential drugs, e.g., estrogen receptor modulators, can also be synthesized de novo or obtained from phage libraries. Phage libraries have been constructed which when infected into host E. coli produce random peptide sequences of approximately 10 to 15 ainio acids [Parmley and Smith, Gene 73:305–318 (1988), Scott and Smith, Science 249:386–249 (1990)]. Once a phage encoding a peptide that can act as a potential drug has been purified, the sequence of the peptide contained within the phage can be determined by standard DNA sequencing techniques. Once the DNA sequence is known, synthetic peptides can be generated which are encoded by these sequences.

These peptides can be selected, for example, for their ability to bind to the estrogen receptor. The selected peptides can then be tested in the methods disclosed herein for their inability to: (1) dissipate a transmembrane pH gradient in a vesicle and/or (2) alter the surface charge on the membrane of the vesicle.

The effective peptide(s) can be synthesized in large quantities for use in in vivo models and eventually in humans to treat a number of diseases such breast cancer, endometriosis, osteoporosis, prostatic hyperplasia, restenosis and to lower cholesterol. Indeed Droloxifene, an analog of tamoxifen, has been reported to be effective in the treatment of breast cancer U.S. Pat. No. 5,047,431; endometriosis, U.S. Pat. No. 30 5,455,275; lowering cholesterol, U.S. Pat. No. 5,426,123; osteoporosis, U.S. Pat. No. 5,254,594; prostatic hyperplasia, U.S. Pat. No. 5,441,986; and restenosis, U.S. Pat. No. 5,384,332.

It should be emphasized that synthetic peptide production is relatively non-labor intensive, easily manufactured, quality controlled and thus, large quantities of the desired product can be produced quite cheaply. Similar combinations of mass produced synthetic peptides have been used with great success [Patarroyo, Vaccine, 10:175–178 (1990)].

Drug screens can be performed by any number of means including using high throughput techniques and biological chip technology such as exemplified in U.S. Pat. No. 5,874,219, Issued Feb. 23, 1999, the disclosure of which is hereby incorporated by reference in its entirety.

pH Measurements:

The pH sensitive fluorophores, FITC and SNARF, can be used to measure the pH within endosomes and the cytosol, respectively. Lysosensor Blue DND-167 is a fluorophore that can be used as an independent probe specifically for calibration of the pH within the lumenal compartment of lysosomes. Both FITC and SNARF are ratio metric dyes. The emission intensity of FITC at 530 nm increases with increasing pH with excitation at 490 nm However, it is unaffected by pH when the fluorophore is excited at 450 nm. Therefore, by taking the ratio of the emission intensities at the two excitation wavelengths, one can obtain a pH value independent of FITC concentration in a particular compartment. FITC is most useful for measurement of pH values from 5.0 to 7.0.

SNARF, when excited at 514 nm, emits at two wavelengths: 570 nm and 630 nm The protonated fluorophore emits at 570 nm and the neutral fluorophore emits at 630 nm Again, the ratio of the two emissions corresponds to a pH value that is independent of the concentration of the dye in that compartment. SNARF can be reliably calibrated over the pH range of 6.2 to 9.0.

The fluorescence of Lysosensor Blue DND-167 is dependent on pH. Lysosensor Blue has a functional group that, when deprotonated, leads to a loss of fluorescence of the molecule. The pK of this group is 5.1. Therefore at pH<5.1, a greater percent of the dye will be protonated and will be fluorescent. There is little fluorescence above pH 5.8. At the end of an experiment, to convert the ratios to pH values the fluorescence emission of each dye can be calibrated with solutions of known pH as exemplified below.

Organelle-specific pH Measurements:

The pH can be measured in selective cellular compartments by targeting ratio metric pH probes to specific organelles. For example, using the confocal microscope, the pH probe SNARF can be excited at 514 nm and its emission recorded simultaneously on two orthogonal PMT's using a 610 nm dichroic a 570/30 nm bandpass filter and a 630 nm longpass filter. Using a epi-fluorescence microscope with a intensified CCD camera, the pH probe FITC can be excited alternately at 450 um and 490 nm and emission recorded with a 520/10 bandpass filter.

pH in the Recycling Endosomes:

The transferrin receptor has been used as a selective probe for the recycling endosome pathway [Fuller and Simons, J. Cell Biol., 103:1767–1779 (1986); Roff et al., J. Cell Biol., 103:2283–2297 (1986); Sipe and Murphy, Proc. Natl. Acad. Sci. USA, 84:7119–7123 (1987); Stoorvogel et al., J. Cell Biol., 106:1821–1829 (1988); Dunn et al., J. Cell Biol., 109:3303–3314 (1989); Mayor et al., J. Cell Biol., 121:1257–1269 (1993); McGraw et al., J. Cell Biol., 155:579–594 (1993)]. After endocytosis, the transferrin is transported through the endosomes and then recycled back to the surface without passage through the lysosomes. Thus, the pH of the recycling endosomes can be selectively monitored by conjugating a pH probe, such as FITC or SNARF, to transferrin [Dunn et al., J. Cell Biol., 109:3303–3314 (1989)].

Recycling Compartment pH Measurement:

The probe FITC bound to transferrin can be used to selectively probe the pH of the endocytic compartment. FITC [Scbmid et al., J. Cell Biol., 108:1291–1300 (1989);

Ghosh and Maxfield, J. Cell Biol., 128:549–561 (1995)]. The cells can be loaded with FITC-transferrin and the pH can be calibrated from the fluorescein isothiocyanate (FITC) fluorescence as described below.

pH in the Lysosomes:

The pH in the lysosomes can be assayed both with light and electron microscopy. Light microscopy: Cells can be incubated with FITC-dextran 10 kD (5 mg/ml) (DME/ HERES) for 30 minutes, washed 4 times with DME/ HERES, incubated for an additional 90 minutes to chase out the endosomes and visualized on a Nikon Diaphot equipped with FITC excitation filters [Yamashiro and Maxfield, J. Cell Biol., 105:2723–2733 (1987)]. The pH can then be calibrated. Alternatively cells can be incubated with Lysosensor Blue as exemplified in U.S. application Ser. No. 09/080,739, filed May 18, 1998, the disclosure of which is hereby incorporated by reference herein in its entirety. Electron microscopy: The cells can be incubated with the weak base DAMP, fixed, probed with an mouse antibody to DNP (cross-reacts with DAMP) and visualized with gold-conjugated anti-mouse antibodies. This can be used to quantify the pH in different cellular organelles [Barasch et al., J. Cell Biol., 107:2137–2147 (1988); Barasch et al., Nature (London), 352:70–73 (1991)].

pH of the Cytoplasm and Nucleoplasm:

The pH within the cytoplasm and nucleoplasm can be selectively probed, for example, by loading these compartments with the ratio metric pH probe SNARF conjugated to dextrans using a procedure referred to as "scrape loading" [McNeil et al., J. Cell Biol., 98:1556–1564 (1984)]. The cells can be plated on polystyrene plates at 50% confluency 24–36 hours before loading with dextrans. The medium is then aspirated off the dishes, and the cells are covered with 50 µL of the SNARF dextran at 10 mg/ml concentration. The cells are then scraped off the polystyrene with a rubber scraper and placed in pre-chilled tubes containing 1 ml of media without serum. The cells can be harvested by spinning at a force of 100 g for 5 minutes. The cytosolic pH can be selectively probed by loading the cytosol with a 70 kD SNARF-conjugated dextran. This dextran is too large to enter into organelles or the nucleus. The nucleoplasmic pH can be probed by loading the cytosol with SNARF conjugated to a 10 kD dextran. This is too large to cross cellular membranes, but can enter the nucleoplasm by diffusion across the nuclear pores. Confocal fluorescence microscopy can be used to prepare optical sections through the cell as exemplified below. The fluorescence intensity of the nucleoplasm and cytoplasm can then be quantified.

Acidification of Cellular Microsomes:

The acidification of cellular microsomes can be assayed spectrophotometrically. Two different approaches which can be used for assaying acidification are exemplified in U.S. application Ser. No. 09/080,739, filed May 18, 1998 (the disclosure of which is hereby incorporated by reference herein in its entirety): (a) acidification of the total microsomal preparation using quenching of acridine orange and (b) acidification of the recycling endosomes by monitoring the fluorescence from a microsomal preparation from cells that had previously endocytosed FITC-transferrin.

In a particular protocol for acidification of the total microsomal preparation using quenching of acridine orange, exemplified below, cells are grown and lysed. The homogenate is centrifuged to remove unbroken cells and nuclei. The supernatant is centrifuged in a discontinuous sucrose gradient and the microsomes are separated and then collected. To monitor acidification of the total microsomal fraction, the quenching of AO fluorescence was monitored essentially as described previously [Barasch et al., Nature 352:70–73 (1991)]. Acidic vesicles accumulate AO to high concentrations resulting in the self quenching of the dye and a decrease of the overall fluorescence. Fluorescence can be measured on an fluorometer with $\lambda_{ex}$=488 nm and $\lambda_{em}$=530 nm. Microsomes were suspended in buffer with 6 µM AO in a cuvet. The ability of vesicles to generate a $\Delta$pH in the presence of a potential agent (or a known agent such as tamoxifen) is then determined by adding the agent to the cuvet, equilibrating, and then adding 1 mM Tris-ATP to begin acidification. 2.5 µM of nigericin can be added, as a control, to dissipate any $\Delta$pH formation after the determination is made. Alternatively, the effects of of a potential agent on vesicles with a pre-existing $\Delta$pH, can be determined by their addition following the addition of Tris-ATP to the vesicles.

Acidification from the recycling endosomal fraction can be monitored by first incubating cells with FITC-transferrin for 30 minutes before lysis and isolation of microsomes. Acidification can be monitored by excitation of the FITC fluorophore at 450 and 488 nm and measuring $\lambda_{em}$=520 nm as described above.

Acidification of Yeast Vacuoles:

As exemplified below, vacuoles from S. cerevisiae can prepared from the protease deficient strain BJ2407 by sequential floatation through 12% and 8% Ficoll 400 cushion as described previously [Roberts et al., Methods Enzymol, 194:644–661 (1991)] with the single modification that 1x protease inhibitor mix and 1 mM DTT is included in each step. Acidification can be measured using AO as described above. For acidification in chloride-free solution, gluconate or glutamate can be used, for example, in the vesicle buffer in place of chloride.

Acidification of E. coli Inverted Membrane Vesicles (InV):

As exemplified below, InV can be prepared from the DH5α strain as described [Simon and Blobel, Cell 69:677–684 (1992)]. Acidification can be measured using AO as described above.

$V_m$ of Yeast Vacuoles:

Oxonol V is a membrane permeable anionic fluorescent probe that accumulates into the inner leaflet of vesicles with positive $V_m$, resulting in quenching of fluorescence. Vacuoles can be suspended in chloride or gluconate vesicle buffer with 1 µM Oxonol V. Fluorescence is measured with a $\lambda_{ex}$=600 nm and $\lambda_{em}$=630 nm. After fluorescence has equilibrated, vacuoles are added and the fluorescence is allowed to re-equilibrate. Then, 1 mM Tris-ATP is added and the resulting positive $V_m$ is manifested in fluorescence quenching.

ATPase Activity of Yeast vATPase:

Vacuoles can be diluted in KCl or K-gluconate vesicle buffer. As exemplified below, each sample was split into two and the potential modulating agent, or known modulating agent (e.g., tamoxifen), or carrier can be added. Each of the resulting samples can again be split into two and either carrier or 100 nM bafilomycin $A_1$ can be added. Next, 2 mM Tris-ATP is added to each sample and the vacuoles are incubated at 30° C. for 15 minutes. The phosphate concentration from ATP hydrolysis, can be measured as exemplified below. The bafilomycin inhibitable ATPase activity was taken as the difference between the ATPase activity of each condition with or without 100 nM bafilomycin $A_1$.

Liposome pH:

The lumenal pH ($pH_L$) of liposomes can be assayed with pyranine, as exemplified below. To prepare pyranine loaded liposomes, lipids supplied in chloroform suspension were dried in a round bottom flask under argon for 2 hours. The lipids were then resuspended in acidic or alkaline liposome buffer containing 0.5 mM pyranine. The suspension was incubated at room temperature overnight, then freeze-thawed 6×. Unilamellar liposomes can be made and external dye can be removed as described below. The pyranine fluorescence is then calibrated as a function of pH. The ratio of the fluorescence emission at $\lambda_{em}$=510 nm is monitored with dual excitation wavelengths of $\lambda_{ex}$=405 nm and $\lambda_{ex}$=455 nm. The pH is then increased by addition of a weak base. The fluorescence is measured after each addition and the pH is measured using a pH meter. A titration curve is then generated as described in the Example, below. Potential modulating agents can then be included and the change in the transmembrane pH gradient is determined. After the determination, 1 μM nigericin can be added to dissipate the remaining pH gradient. The $pH_L$ is calculated using the equation pH=x*log($\lambda_{ex}$=405 nm/$\lambda_{ex}$=405 nm)+c, were x and c are constants from the least square fit of the titration curve.

Liposome Chloride Concentration:

Lucigenin is a fluorescent dye that is collisionally quenched by chloride and other halides, but not by nitrate [Biwersi, et al., *Analytical Biochemistry* 219:139–143 (1994)]. Unilamellar liposomes are made and external dye is removed as described below. The fluorescence of lucigenin is then calibrated as a function of chloride as exemplified below. The liposomes are diluted in buffer with 1 μM tributyltin (TBT) a Cl⁻—OH⁻ exchanger, and 1 μM nigericin, a K⁺—H⁺ exchanger. This results in rapid net dissipation of KCl gradient. Aliquots of different concentrations of KCl are added and lucigenin fluorescence ($\lambda_{ex}$=370 nm/$\lambda_{ex}$=505 nm) is recorded. The fluorescence is fitted to the Stern-Volmer equation: $F_0/F=1+k[Cl]$, where $F_0$ is the fluorescence in the absence chloride. To measure the chloride permeability, the fluorescence is followed in liposomes after the addition of 50 mM KCl. After 10 minutes, 1 μM TBT, and 1 μM nigericin are added. The chloride concentration is calculated using the Stern-Volmer equation with k calculated from the titration curve.

Membrane Surface Charge Determinations:

Membrane surface charge determinations can be performed on the membranes of vesicles, as defined herein, or on planar lipid bilayers. Methods for measuring electrostatic potentials of membranes have been described [see, Cafiso et al., *Methods of Enzymology* 171:342–364 (1989); and Rottenbreg, *Methods of Enzymology* 171:364–387 (1989), the contents of which are hereby incorporated by reference herein in their entireties].

Electrophoretic Mobility:

Electrophoretic mobility can be applied to pure liposomes or isolated mitochondria Liposomes are made with some charged phospholipids. The rate at which the liposomes move in an electric field is proportional to the charge on the surface of the liposomes. Agents that bind to the liposomes, thereby increasing or decreasing the surface charge, increase or decrease the rate of movement of the liposomes.

Conductance of Carriers Across a Membrane:

The conductance of a planar bilayer to FCCP is in response to the transmembrane potential. It responds to the sum of the transmembrane potential measured in bulk solution and the surface potentials on each membrane. Screening the surface charges affects the conductance to FCCP. This technique works very cleanly in planar lipid bilayers.

Adsorption of Ions to Membranes:

(1) Shift in the Fluorescence of a pH Probe Bound to the Surface.

Negative charges on the surface of the membrane will attract protons and positive charges will repel protons. Thus, membrane surface charges will change the local pH around probes bound to the surface of the membrane. If a fluorescent pH sensitive probe, such as a lipid coumarin dye, is bound to the membrane, the fluorescence of the dye is an indicator of the surface charge. Adding potential modulating agents that shift the surface charge will shift the fluorescence.

(2) Quenching Fluorescent Acridines:

The fluorescence of the positively charged acridine molecules is quenched as it aggregated near a membrane surface. This has been used to measure the surface charge in various organelles such as chloroplasts. Potential modulating Agents that shift the surface charge shift the fluorescence.

(3) NMR:

$^{31}P$ NMR measurements of a paramagnetic cation such as Manganese can be used to sense the potential at the phosphodiester group of the lipid at the membrane surface in the presence and absence of the potential modulating agents.

(4) Fluorescence:

The anion TNS [2-(p-toluidinyl)naphthalene 6 sulfonate] accumulates near positively charged membranes and can be used as a probe of surface charge in the presence and absence of the potential modulating agents.

(5) Electron Spin Resonance:

ESR is performed on spin labeled ions to assay the effects of screening surface charges on accumulation of the spin probe near the membrane in the presence and absence of the potential modulating agents.

In vitro Estrogen Receptor Binding Assay:

Receptor Preparation:

CHO cells overexpressing the estrogen receptor can be grown in 150 mm.sup.2 dishes in DMEM+10% dextran coated charcoal, stripped fetal bovine serum. The plates are washed (e.g., twice with PBS and once with 10 mM Tris-HCl, pH 7.4, 1 mM EDTA). Cells are harvested by scraping the surface and then the cell suspension is placed on ice. Cells are then disrupted with a hand-held motorized tissue grinder using two, 10-second bursts. The crude preparation is centrifuged at 12,000 g for 20 minutes followed by a 60 minute spin at 100,000 g to produce a ribosome free cytosol. The cytosol is then frozen and stored at −80° C. The protein concentration of the cytosol can be estimated using the BCA assay for example with reference standard protein. The Binding assay conditions: A competition assay between potential estrogen receptor modulators and labled-estradiol (e.g., radioactive) can be performed in a 96-well plate (polystyrene). Counts per minute (CPM) of radioactivity can be automatically converted to disintegrated per minute (DPM) by the Beckman LS 7500 Scintillation Counter using a set of quenched standards to generate a H# for each sample. To calculate the % of estradiol binding in the presence of 100 or fold 500 fold competitor the following formula can be applied: [(DPM sample-DPM not removed by charcoal/(DPM estradiol-DPM not removed by charcoal)] times 100%=% of estradiol binding. For the generation of IC.sub.50 curves, % binding is plotted vs compound. see Hulme, E. C., ed. 1992. *Receptor-Ligand Interactions: A Practical Approach.* IRL Press, New York. (see especially chapter 8).

Labeling and pH Measurements

Cells and cellular vesicular compartments can be labeled with any number of pH-sensitive compounds for the practice of the present invention. A list of such compounds has been compiled by Parent Fluorophore and is available at the internet address http://www.probes.com/handbook/ch23-toc.html. Below are examples of such compounds and methodologies which can be used but are no way meant to limit the compounds or methodologies that can be employed by the present invention. Appropriate pH indicators for fluorescence microscopy include but in no way is limited to the use of any vital pH-indicator, acridine orange, Lysosensor Blue DND-167, SNAFL, SNARE, BCECF, FITC, and DAMP and green fluorescent protein. Appropriate pH indicators for confocal microscopy include but in no way is limited to any vital pH-indicator, acridine orange, Lysosensor Blue DND-167, SNAFL. Below the pH range and relevant excitation/emission information is provided for a few of such fluorescent labels:

SNAFL indicators: pH 7.2–8.2;
  Excitation ratio 490/540 nm or Emission ratio 540/630 nm
SNARF indicators: pH 7.0–8.0:
  Emission ratio 580/640 nm
HPTS (pyranine): pH 7.0–8.0
  Excitation ratio 450/405 nm
BCECF: pH 6.5–7.5
  Excitation ratio 490/440 nm
Fluoresceins and carboxyfluoresceins: pH 6.0–7.2
  Excitation ratio 490/450 nm
Oregon Green dyes: pH 4.2–5.7
  Excitation ratio 510/450 nm or excitation ratio 490/440 nm
Rhodols (including NERF dyes): pH 4.06.0
  Excitation ratio 514/488 nm or excitation ratio 500/450 nm
Lyso Sensor probes: pH 3.5–8.0 *
  Excitation ratio 340/380 nm Additional potentially suitable labels include enzymes, pH-sensitive fluorophores as described in the Example below, as well as other fluorophores such as (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), and chemiluminescent agents. When a control marker is employed, the same or different labels may be used for the test and control marker gene.

In the instance where a radioactive label, such as the isotopes $^3H$, $^{14}C$, 32P, 35S, $^{36}Cl$, $^{51}Cr$, 57Co, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimnulation, e.g. U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932 and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety including a green fluorescent protein and its derivatives as described in U.S. Pat. No. 5,625,048 filed Apr. 29, 1997 and WO 97/26333, published Jul. 24, 1997 the disclosures of which each are hereby incorporated by reference herein in their entireties; or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology*, 70:419–439 (1980) and in U.S. Pat. No. 4,857,453. Suitable enzymes include, but are not limited to, alkaline phosphatase, β-galactosidase, luciferase, horseradish peroxidase. Other labels for use in the invention include magnetic beads or magnetic resonance imaging labels.

Pharmaceuticals

The present invention also provides methods for treating diseases, such as breast cancer. One such embodiment consists of administering to a patient (human or animal) an agent identified by a method of the present invention in an amount effective for treating the patient (or animal). According to the invention, the agent can be part of a therapeutic composition which could also contain a chemotherapeutic agent. The therapeutic composition may be introduced parenterally, e.g., via intravenous injection, and also including, but is not limited to, intra-arteriole, intramuscular, intradermal, subcutaneous, intraperitoneal, intraventricular, and intracranial administration. transmucosally, e.g., orally, nasally, or rectally, or transdermally. In the case when the agent is an analog of tamoxifen, the vast experience in administering that drug may, of course, be used in the administration of such an analog.

In another embodiment, the therapeutic composition can be delivered in a vesicle, in particular a liposome [see Langer, *Science* 249:1527–1533 (1990); Treat et al., in *Liposomes in the Therapy of Infectious Disease and Cancer*, Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing the agent.

In yet another embodiment, the therapeutic compound can be delivered in a controlled release system. For example, the agent may be adnntstered using intravenous infusion, an implantable osmotic pump, a transdermal patch, liposomes, or other modes of administration. In one embodiment, a pump may be used [see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of the therapeutic target, i.e., the tissue of interest, thus requiring only a fraction of the systemic dose [see, e.g., Goodson, in *Medical Applications of Controlled Release*, supra, vol. 2, pp. 115–138 (1984)]. Preferably, a controlled release device is introduced into a subject in proximity of the site of a tumor.

Other controlled release systems are discussed in the review by Langer [Science 249:1527–1533 (1990)].

A subject in whom administration of the agent is an effective therapeutic regimen is preferably a human, but can be any animal, preferably a mammal. Thus, as can be readily appreciated by one of ordinary skill in the art, the methods and pharmaceutical compositions of the present invention are particularly suited to administration to any animal, particularly a mammal, and including, but by no means limited to, domestic animals, such as feline or canine subjects, farm animals, such as but not lmited to bovine, equine, caprine, ovine, and porcine subjects, wild animals (whether in the wild or in a zoological garden), research animals, or for veterinary medical use.

In yet another aspect, the present invention provides pharmaceutical compositions comprising the modulating agents identified/selected by the methods described above. Such pharmaceutical compositions may be for administration for injection, or for oral, pulmonary, nasal or other forms of administration. In general, comprehended by the invention are pharmaceutical compositions comprising an agent that can be administered with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodiumrn etabisulfite), preservatives (e.g., Thimersol, benzyl alcohol) and bulkng substances (e.g., lactose, mannitol); incorporation of the material into particulate preparations of polymeric compounds such as polylactic acid, polyglycolic acid, etc. or into liposomes. The compositions may be prepared in liquid form, may be in dried powder, such as lyophilized form. Alternatively, the agent can be administered in a pill.

Kits

The present invention also includes kits for practicing the present invention. One such kit comprises a vesicle of the present invention and a labeled probe that can be used to measure the transmembrane pH gradient. Another embodiment comprises a vesicle of the present invention and a probe useful for determining the surface charge on the membrane of the vesicle. In a preferred embodiment, a protocol is included describing a method of determining the transmembrane pH gradient of the vesicle and/or the dissipation of the same; and/or a method of determing the surface charge on the membrane of the vesicle. In another embodiment, a sample of tamoxifen or other known estrogen receptor modulator is included as a control. Any of the pH probes of the present invention can be included, and any of the vesicles also can be supplied as part of the kits.

The present invention may be better understood by reference to the following non-limiting Example, which is provided as exemplary of the invention. The following example is presented in order to more fully illustrate the preferred embodiments of the invention. It should in no way be construed, however, as limiting the broad scope of the invention.

EXAMPLE

A Mechanism for Tamoxifen Mediated Inhibition of Acidification

Summary

Recently, it was observed that tamoxifen inhibits acidification of intracellular organelles of both estrogen receptor positive and negative cell lines [Altan et al., *Proc. Natl Acad Sci U.S.A.* 96:4432–4437 (1999)]. This inhibition of acidification may be a mechanism for many of the effects of tamoxifen. For example, the effects of tamoxifen on osteoporosis [Sundquist et al., *Biochemical & Biophysical Research Communications* 168:309–313 (1990)], vesicular transport [Gekle et al., *American Journal of Physiology* 268:F899–F906 (1995); van Weert et al., *J. Cell Biol.* 130:821–834 (1995)], or multidrug-resistance [Altan et al., *J.Exp.Med*, 187:1583–1598 (1998); Hurwitz et al., *Blood* 89:3745–3754 (1997)] are mimicked by blocking the protonvacuolar ATPase (vATPase) or by a protonophore.

As described below, the mechanism(s) by which tamoxifen inhibits ATP dependent in vitro acidification of organelles isolated from tissue culture cells, whole tissue, vacuoles from *S. cerevisiae*, and inverted vesicles isolated from *E. coli* has been investigated. The studies on yeast vacuolar acidification demonstrate that tamoxifen decreased both ATP generated pH gradients and $V_m$ but increased the ATPase activity of the vATPase. These results indicate that tamoxifen affects ion permeability of a variety of biological membranes through interaction with either membrane proteins or the lipid bilayer.

The possibility that tamoxifen acts directly on the lipid bilayer was addressed with studies of pure lipid vesicles in which tamoxifen increased the rate of dissipation of the pH gradient. The data indicates that this occurs by two distinct mechanisms. First, tamoxifen is a lipophilic weak base with a neutral form that can readily flip-flop between membranes and a basic form that is relatively impermeable. Thus, tamioxifen would accumulate in acidic vesicles, bind protons and increase lumenal pH. Importantly, tamoxifen is over 1000-fold more potent in increasing lumenal pH than the soluble weak base ammonium chloride. This may be explained by the predominent partitioning of tamoxifen into the lipid phase, increasing the effective concentration. However, this mechanism can only be involved in dissipation of a pH gradient when the lumen is acidic. Secondly, tamoxifen can mediate coupled transport of proton or hydroxide with chloride based on the following observations: 1) It mediates electroneutral dissipation of pH gradients that is dependent on the presence of chloride or other halides; 2) it mediates an increased dissipation rate of chloride gradients; and 3) it mediates net proton influx when the external chloride concentration is greater than the lumenal chloride concentration.

Acidification is crucial for the proper functioning of many cellular processes and its disruption may account for many of the pleiotropic effects described for tamoxifen. The results presented here show that at low micromolar concentrations, tamoxifen can inhibit acidification and dissipate pH gradients in a variety of in vitro systems. While this concentration is higher than required to modulate the estrogen receptor, it is similar to those reported for many estrogen receptor independent effects. Importantly, this concentration can readily be achieved in the clinic. The elucidation of a biochemical mechanism for this estrogen receptor independent activity of tamoxifen significantly contributes to the design of modulators of the estrogen receptor that lack these side-effects.

Materials and Methods

Materials:

Bafilomycin $A_1$, monensin, Acridine Orange (AO), pyranine: (8-hydroxypyrene-1,3,6-trisulfonic acid), tamoxifen, Tris-ATP and nigericin were from Sigma (St. Louis, Mo.). BODIPY$^\zeta$-transferrin, lucigenin, p-xylene-bis-pyridinium bromide (DPX), were from Molecular Probes (Eugene, Oreg.). Adriamycin was from Calbiochem (La Jolla, Calif.). Concanomycin A was from Fluka (Milwaukee, Wis.) .Palmitoyl-oleoyl-phosphatidylcholine (POPC) and cholesterol was from Avanti Polar (Alabaster, Ala.).

Acidification of Cellular Microsomes:

Cells were grown in Minimal Essential. Medium supplemented with 10% Fetal Bovine Serum to confluence in 10 level Cell Factories (Nunc, Naperville, Ill.), trypsinized, washed 3× with cold PBS and lysed with a Dounce homogenizer (Pestle A) in 0.25 M sucrose, 20 mM HEPES (pH 7.4), 1 mM DTT, 1 mM EDTA, and 1× protease inhibitor mix (1 µg/ml leupeptin, 1 µ/ml pepstatin A, 1 µg/ml aprotinin, and 16 µM PMSF mixed to 100× before use). The homogenate was centrifuged twice for 10 minutes at 3000×g to remove unbroken cells and nuclei. The supernatant was layered over 20 ml of 0.5 M sucrose (20 mM HEPES (pH 7.4), 1 mM DTT, 1 mM EDTA, 1× protease inhibitor mix) and 1 ml of 2 M sucrose and centrifuged for 1 hour at 100,000 g (Beckman Ti60 Rotor). Microsomes are collected at the 0.5M and 2M interface.

To monitor acidification of the total microsomal fraction, the quenching of AO fluorescence was monitored essentially as described previously [Barasch et al., Nature 352:70–73 (1991)]. Acidic vesicles accumulate AO to high concentrations resulting in the self quenching of the dye and a decrease of the overall fluorescence. Fluorescence was measured on an SLM Aminco-Bowman series 2 luminescence spectrometer with $\lambda_{ex}$=488 nm and $\lambda_{em}$=530 nm Microsomes (80 µg protein) were suspended in 2.5 ml vesicle buffer (125 mM KCl, 5 mM MgCl$_2$, 20 mM HEPES (pH 7.4), 1 mM DTT, 1 mM EDTA, 2 mM NaN$_3$), with 6 µM AO (5 mM stock in H$_2$O) in a cuvet. To examine the ability of vesicles to generate a ΔpH in the presence of tamoxifen or bafilomycin A$_1$, 0, 1, 2, 4, or 8 µM tamoxifen (10 mM stock in EtOH) or 10 mM bafilomycin A$_1$ (10 mM stock in 10% DMSO) was added. After equilibration for 30 minutes at 25° C. 1 mM Tris-ATP was added to begin acidification (100 mM stock, titrated to pH 7.4 with 1 M Tris-base before use). Twenty minutes later, 2.5 µM of nigericin (10 mM stock in EtOH) was added to dissipate any ΔpH formation. To study the effects of tamoxifen and bafilomycin A$_1$ on vesicles with a pre-existing ΔpH, tamoxifen or bafilomycin A$_1$ were added 10 minutes after the addition of Tris-ATP.

Acidification from the recycling endosomal fraction was monitored by first incubating cells with FITC-transferrin for 30 minutes before lysis and isolation of microsomes. Acidification was monitored by excitation of the FITC fluorophore at 450 and 488 nm and measuring $\lambda_{em}$=520 nm as described previously.

Acidification of Yeast Vacuoles:

Vacuoles from *S. cerevisiae* were prepared from the protease deficient strain BJ2407 (Yeast Genetic Stock Center, University of California, Berkeley) by sequential floatation through 12% and 8% Ficoll 400 cushion as described previously [Roberts et al., *Methods Enzymol*, 194:644–661 (1991)] with the single modification that 1× protease inhibitor mix and 1 mM DTT was included in each step. This procedure produced a 25-fold enrichment of the vacuolar marker α-mannosidase. Acidification was measured using AO as described above. For acidification in chloride-free solution, gluconate or glutamate was used in vesicle buffer instead of chloride.

Acidification of *E. coli* Inverted Membrane Vesicles (InV):

InV were prepared from the DH5α strain as described [Simon and Blobel, *Cell* 69:677–684 (1992)]. Acidification was measured using AO as described above.

$V_m$ of Yeast Vacuoles:

Oxonol V is a membrane permeable anionic fluorescent probe that accumulates into the inner leaflet of vesicles with positive $V_m$, resulting in quenching of fluorescence. Vacuoles were suspended in chloride or gluconate vesicle buffer with 1 µM Oxonol V. Fluorescence was measured with a $\lambda_{ex}$=600 nm and $\lambda_{em}$=630 nm. After fluorescence has equilibrated, vacuoles were added and the fluorescence is allowed to re-equilibrate. Then, 1 mM Tris-ATP was added and the resulting positive $V_m$ was manifested in fluorescence quenching.

ATPase Activity of Yeast vATPase:

Vacuoles were diluted in KCl or K-gluconate vesicle buffer. Each sample was split into two and either 5 µM tamoxifen or carrier was added. Each of the four resulting samples was again split into two and either carrier or 100 mM bafilomycin A$_1$ was added. Next, 2 mM Tris-ATP was added to each sample and the vacuoles were incubated at 30° C. for 15 minutes. To measure the phosphate concentration from ATP hydrolysis, equal volume of Taussky-Shorr Reagent (1% w/v ainmoniummolybdate (w/v), 2.7% v/v sulfuric acid, and 5% w/v ferrous sulfate hexahydrate) was added and the samples were developed for 15 minutes. The $A_{660}$ was measured (Spectronic Genesys 2) which is linearly related to phosphate concentration. The bafilomycin inlubtable ATPase activity was taken as the difference between the ATPase activity of each condition with or without 100 nM bafilomycin A$_1$.

Liposome pH:

The lumenal pH (pH$_L$) of liposomes was assayed with pyranine, a fluorescent dye with a pK$_a$~7.3 and a $\lambda_{ex}$=405 nm in its acid form (−3 charge) and a $\lambda_{ex}$=455 nm in its basic form (−4 charge). To prepare pyranine loaded liposomes, lipids (2 mg POPC, 1 mg cholesterol) supplied in chloroform suspension were dried in a round bottom flask under argon for 2 hours. The lipids were then resuspended in acidic or alkaline liposome buffer (300 mM KCl, 20 mM MES, 20 mM MOPS, 20 mM Tricine titrated with KOH to either pH 6.2 or pH 8.1) containing 0.5 mM pyranine. The suspension was incubated at room temperature overnight, then freeze-thawed 6×. Unilamellar liposomies were prepared by extrusion 3× through 2 stacked 100 nm Nucleopore (Corning/Costar Scientific, Acton, Mass.) polycarbonate filters in an Avestin (Vancouver, BC) extruder at 600 PSI. More than 95% of external pyranine was separated from the liposomes by sequentially runing through a NAP-10 and NAP-25 desalting columns (Pharmacia, Piscataway, N.J.). Internal pyranine leakage was <1% per day and liposomes were used within one week of preparation.

Figure 5:
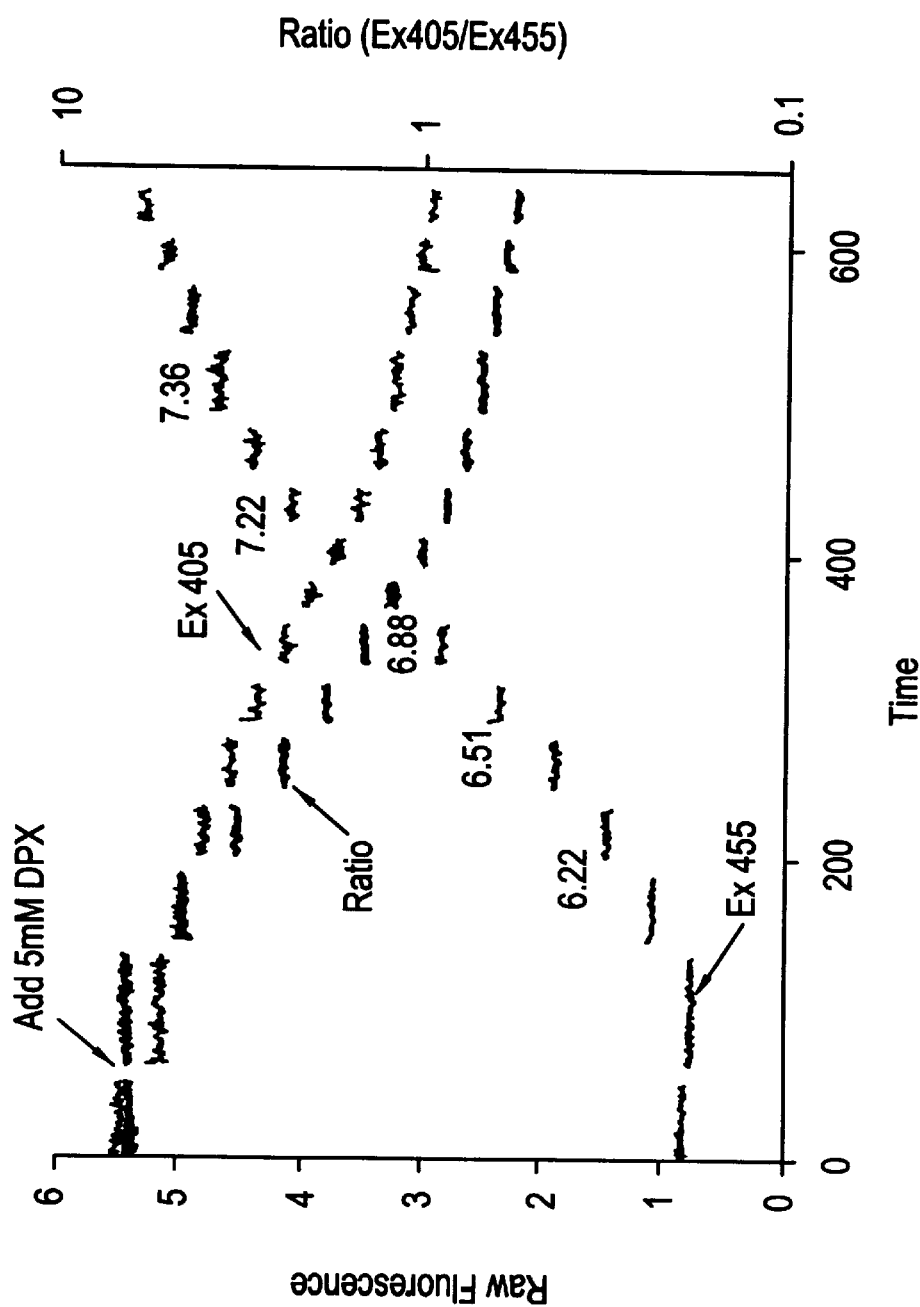
FIG. 5 shows the titration curve of pyranine loaded liposomes. Pyranine is a non-membrane permeable ratiometric pH indicator. Its acidic form is fluorescent when excited at 405 nm and its basic form is fluorescent when excited at 455 nm Liposomes ($pH_{in}$=6.3) were loaded with pyranine and diluted into buffer with $pH_{out}$=6.3 in the presence of nigericin, to allow rapid equilibration between internal and external pH. The raw fluorescence when excited at 405 and 455 (left axis) as well as the ratio (right axis, log scale) were monitored. DPX, a non-permeable quencher of pyranine fluorescence was added and decreased the raw fluorescence by only the dilution factor, indicating that virtually all pyranine fluorescence is from the liposome lumen. Aiquots of MES were added to decrease the external pH and internal pH (due to the presence of nigericin) and the pH was measured using a pH meter. There was no decrease in total fluorescence tbroughout the experiment, indicating no dye leakage or DPX influx.

The pyranine fluorescence was calibrated as a function of pH by diluting the liposomes with pH 6.2 into a weakly buffered solution of identical pH (300 mM KCl, 1 mM MES, 1 mM MOPS, 1 mM Tricine, pH 6.2), 1 µM nigericin to allow rapid equilibration with external pH and 5 mM DPX to quench external pyranine. The ratio of the fluorescence emission at $\lambda_{em}$=510 nm was monitored with dual excitation wavelengths of $\lambda_{ex}$=405 nm and $\lambda_{ex}$=455 nm. Sequential aliquots of 0.1 mM glycylglycine, pH 8.4 were added to increase pH (See FIG. 5). The fluorescence was measured after each addition and the pH was measured using a pH meter. The logarithm of the fluorescence ratio was linearly dependent on the pH. The curve generated by a least square fit between pH 6.2 and 7.9 resulted in $\chi^2$>0.99. The cahiration curve for the liposomes of lumenal pH 8.1 was generated identically except sequential aliquots of 0.1 mM K-MES pH 5.0 were added for titration and the curve was generated between pH 8.1 and pH 6.4.

To measure the rate of pH dissipation of liposomes with lumenal pH=6.2, the liposomes were diluted in weakly buffered solution of identical pH as described above, but with no nigericin. Various agents (tamoxifen, valinomycin, FCCP) were included as described in the text. The external pH was shifted to pH 7.3 by addition of 5 mM glycylglycine pH 8.4 and the fluorescence ratio monitored. After 10 minutes, 1 μM nigericin was added to dissipate the remaining pH gradient. The $pH_L$ was calculated using the equation $pH=x*\log(\lambda_{ex}=405 \text{ nm}/\lambda_{ex}=405 \text{ nm})+c$, were x and c are constants from the least square fit of the titration curve. To measure the rate of pH dissipation of liposomes with $pH_L=8.1$, the identical procedure was followed except 5 mM K-MES pH 5.0 was added to shift the external pH to 6.9.

To assay the effect of addition of $NH_4Cl$ or tamoxifen on liposome pH, liposomes with $pH_L=6.2$ were diluted into identical buffer (300 mM KCl, 20 mM MES, 20 mM MOPS, 20 mM Tricine pH 6.2) containing 5 mM DPX and the fluorescence ratio was followed after addition of $NH_4Cl$ or tamoxifen.

Liposome Chloride Concentration:

Lucigenin is a fluorescent dye that is collisionally quenched by chloride and other halides, but not by nitrate [Biwersi, et al.; Analytical. Biochemistry 219:139–143 (1994)]. Lipids dried as described above were rehydrated in 300 mM $KNO_3$, 10 mM K-HEPES pH 7.3 and 0.5 mM lucigenin. 100 nm unilamellar liposomes were made and external dye was removed as descrnbed above.

To calibrate the fluorescence of lucigenin as a function of chloride, the liposomes were diluted in buffer (300 mM $KNO_3$, 10 mM K-HEPES pH 7.3) with 1 μM tributyltin (TBT) a $Cl^-$—$OH^-$ exchanger, and 1 μM nigericin, a $K^+$—$H^+$ exchanger. This results in rapid net dissipation of KCl gradient. Aliquots of 0.5 mM, 1 mM, 2 mM, 4 mM, 8 mM, 16 mM, and 32 mM KCl were added and lucigenin fluorescence ($\lambda_{ex}=370$ nm/$\lambda_{ex}=505$ nm) was recorded. The fluorescence was fitted to the Stem-Volmer equation: $F_0/F=1+k[Cl]$, where $F_0$ is the fluorescence in the absence chloride.

To measure the chloride permeability, the fluorescence was followed in liposomes after the addition of 50 mM KCl. After 10 minutes, 1 μM TBT, and 1 μM nigericin was added. The chloride concentration was calculated using the Stern-Volmer equation with k calculated from the titration curve.

Octanol Partitioning of Tamoxifen:

The concentration of tamoxifen was measured by its absorbance peak at 245 nm. The $OD_{245}$ of 20 μM tamoxifen in PBS, HCl, pH 1, or pH 13 KOH solution was acquired. Then, 1 μL of octanol was added, the solution was vortexed, and the $OD_{245}$ of the aqueous phase was acquired.

Results

In vitro Acidification of Vesicles from Mammalian Cells

Total Microsomal Preparation:

The mechanism by which tamoxifen inhibited acidification of intracellular organelles was first addressed by testing whether tamoxifen acted directly on the organelles or indirectly through soluble modulators. Acidification of organelles was assayed in vitro using microsomes isolated from MCF-7/ADR cells that are free of detectable soluble cytosolic proteins.

Acridine orange (AO) was used as a probe for lumenal acidification. As vesicles acidify, they accumulate AO to self-quenching concentrations, and deplete the extra-vesicular free AO, resulting in a decrease in total fluorescence. Acidification was initiated by the addition of ATP to a purified microsomal fraction in the absence of cytosol (FIG. 1A, at t=300 sec). Over the subsequent 1200 seconds, there was a reduction of the AO fluorescence, suggesting an accumulation of AO within the lumen of the microsomes. Nigericin, a $K^+/H^+$ exchanger that rapidly dissipates pH gradients, was added at the end of each reaction (t=1500 seconds). In all experiments the AO fluorescence returned to its pre-ATP levels. This indicates that the decreased fluorescence was the consequence of the generation of a pH gradient.

When MCF-7/ADR vesicles were pre-treated with tamoxifen for 30 minutes, there was a dose-dependent inhibition of AO quenching (FIG. 1A). Inhibition was evident when using 1 μM tamoxifen and acidification was totally blocked with 8 μM tamoxifen. To quantify the effects of tamoxifen on acidification, acidification was plotted (as assayed by quenching of AO fluorescence) as a function of tamoxifen concentration (FIG. 1A, Inset). The $ID_{50}$ for maximal quenching is approximately 3 μM, which is in the same range that tamoxifen inhibits acidification in vivo [Altan et al., Proc Natl Acad Sci U.S.A. 96:4432–4437 (1999)]. Bafilomycin $A_1$ was employed as a positive control. Bafilomycin $A_1$, is a potent and specific inhibitor of the vATPase responsible for acidification of all intracellular compartments [Bowman et al., Proc.Natl.Acad.Sci. USA 85: 7972–7976 (1988)].

Figure 1B:
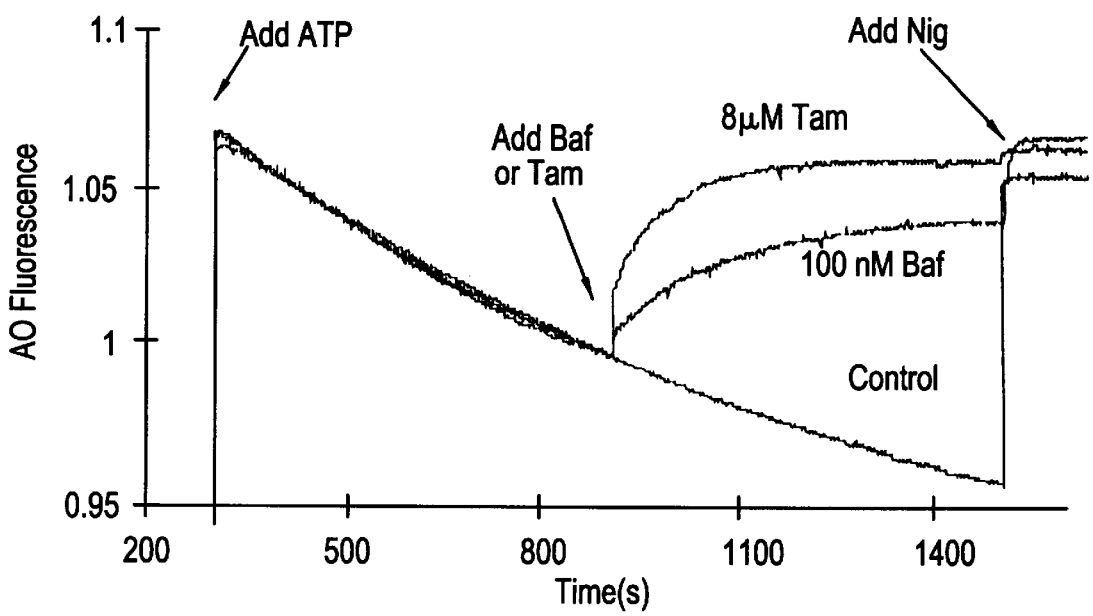

To determine the time course for the inhibition of acidification by tamoxifen, it was added 10 minutes after addition of ATP (FIG. 1B). Addition of tamoxifen rapidly reversed acidification and caused an almost complete dissipation of the pH gradient within 5 minutes. Addition of bafilomycin $A_1$ dissipated the pH gradient at a much slower rate, even when used at 100 nM, which is ten times the concentration that blocked 95% of acidification (see FIG. 1A). Addition of nigericin (FIG. 1B) and monensin dissipated the pH gradient significantly faster than tamoxifen. Thus, the time course of alkalinization by tamoxifen is distinguishable from both rapidly acting electroneutral protonophores and inhibitors of the vATPase.

The fact that the in vitro acidification assay used purified microsomes in the absence of cytosolic or nuclear components indicates that the effects of tamoxifen on pH should be independent of cytosolic factors, such as the estrogen-receptor, and of both transcription and translation. In addition, tamoxifen had similar effects on in vitro acidification of microsomes isolated from liver and kidney tissue from mice. Therefore, the effect of tamoxifen on organelle acidification appears to be a general phenomenon.

Figure 1C:
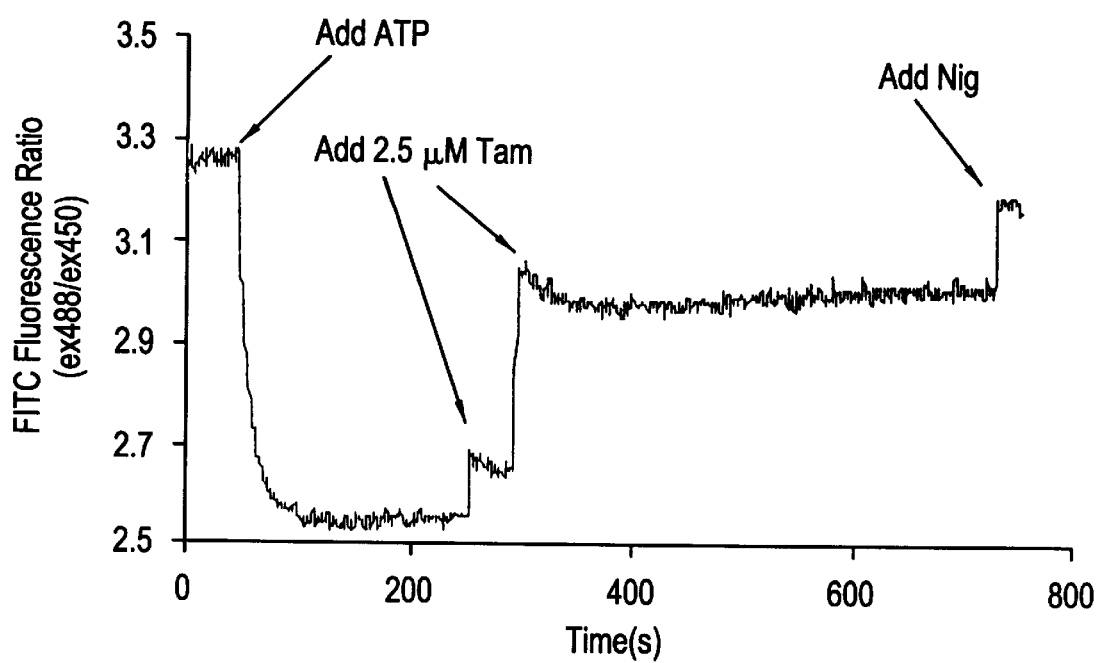

In vitro Acidification of Recycling Endosomes:

To specifically examine the acidification of the endosomes in vitro, in vitro acidification was assayed using FITC-transferrin which is constrained by the transferrin receptor to the endocytic pathway. MCF-7/ADR cells were incubated with FITC-transferrin before lysis and isolation of microsomes. Since this assay is not based on the redistribution of probes, it further serves as verification that AO quenching resulted from vesicular acidification. Upon addition of ATP, there was a decrease in the ratio of the FITC-emission (FIG. 1C). This signal was the consequence of acidification, since it was reversed upon the addition of nigericin. The addition of 2.5 μM tamoxifen partially reversed the acidification in these organelles. This was farher reduced by raising the tamoxifen concentration an additional 2.5 μM. These results indicate that the recycling endosomes were one of the compartments in this in vitro assay whose acidification was blocked by tamoxifen.

Mechanisms of Organelle Acidification:

Acidification of intracellular organelles utilizes an electrogenic proton pump (the vATPase) and chloride channels [Glickman et al., *J.Cell Biol.* 97:1303–1308 (1983); Mellman et al., *Annu.Rev.Biochem.* 55:663–700 (1986)]. The vATPase couples ATP hydrolysis to proton movement. The unidirectional movement of the proton generates an inside positive $V_m$ which limits acidification. The chloride channels allow passive chloride influx into the organelles, dissipating the $V_m$. Tamoxifen could inhibit acidification by the following possible mechanisms: (1) direct inhibition of the vATPase; (2) indirect inhibition of the vATPase through modulation of the $V_m$ (such as blocking a chloride conductance); (3) inhibition of acidification by a weak base effect; or (4) dissipation of pH gradients as a protonophore.

There exists evidence in support of each of these mechanisms: (1) Inhibition of the vATPase. Tamoxifen has been reported to inhibit acid secretion by avian osteoclasts through inhibition of the plasma membrane vATPase activity. This activity has been attributed to the antagonism by tamoxifen of the membrane bound calnodulin-dependent cyclic nucleotide phosphodiesterase, which regulates the vATPase [Williams et al., *Journal of Cellular Biochemistry* 66:358–369 (1997)]. (2) Inhibition of the chloride channel. Tamoxifen has been reported to inhibit the volume activated chloride channel [Zhang et al., *Journal of Clinical Investigation* 94:1690–1697 (1994)]. (3) Dissipation of pH gradient by a weak base effect. A weak base (such as ammonium chloride) will rapidly cross the membrane in a neutral (i.e. $NH_3$) form and bind protons in the interior causing an alkaline shift. The charged form of these molecules will accumulate according to the Henderson-Hasselbach equilibrium. Tamoxifen is a weak base with a $pK_a$ of 6.9 when measured by NMR in 10% Triton solution [Bottega and Epand, *Biochemistry* 31:9025–9030 (1992)]. At a free tamoxifen concentration of 8 μM, a pH 7.3–5.3 pH gradient will result in <200 μM lumenal concentration. This is less than the buffering capacity of the organelles and this should not significantly perturb lumenal pH. Thus, this mechanism initially appeared unlikely. (4) Dissipation of pH gradient by increasing proton permeability. Tamoxifen partitions into lipids, increases membrane fluidity, and decreases lipid peroxidation [Wiseman et al., *FEBS Letters* 330:53–56 (1993)]. If the charged protonated form of tamoxifen were membrane permeable, tamoxifen would act like a classic protonophore. This mechanism has been proposed for the ability of many amine local anesthetics to uncouple respiration [Garlid and Nakashima, *J.Biol.Chem.* 258:7974–7980 (1983); Sun and Garlid, *J.Biol.Chem.* 267:19147–19154 (1992)].

Each of these potential mechanisms has distinct consequences for ATPase activity and $V_m$ of the acidic organelle (Table 1).

TABLE 1

Predicted Effects of Potential Mechanisms of Tamoxifen on $V_m$ and ATPase Activity

|  | $V_m$ | ATPase activity |
|---|---|---|
| Inhibit H-ATPase | Decrease | Decrease |
| Block counter-ion transport | Increase | Decrease |
| Increase proton permeability | Decrease | Increase |
| Weak base effect | Same to slight Increase | Slight Increase |

If tamoxifen initbits the vATPase, it would decrease the ATPase activity. In addition, it should decrease $V_m$ of the organelles since the proton pumping is generating the $V_m$. If taroxifen inhibits the chloride channel, it would increase $V_m$, since the chloride channel serves to dissipate $V_m$. As a consequence of the increased $V_m$, the vATPase cannot pump protons, resulting in a decreased rate of ATP hydrolysis. If tamoxifen is a protonophore, it should decrease $V_m$ by allowing protons to permeate and increase ATPase activity by decreasing the electrochemical gradient against which the vATPase must pump. A weak base should slightly increase $V_m$ and ATPase activity since it dissipates the proton gradient in favor of an electrical gradient.

The predictions of these mechanisms were tested on isolated vacuoles from Saccharomyces cerevisiae. Vacuoles from *S. cerevisiae* offer three particular advantages in biochemical studies of the actions of tamoxifen. (i) They further address the specificity of the effects of tamoxifen (*S. cerevisiae* are known not to have an estrogen receptor). (ii) They use the same basic machinery as mammalian organelles, a vATPase and chloride channel, to generate the proton gradient. (iii) They can be purified in large quantities. It is very difficult to prepare mammalian organelles to the high purity required to assay $V_m$ and ATPase activity. In yeast vacuole preparations, the vATPase represents ~50% of all ATPase activity, which is much higher than attainable for endosome or Golgi preparations.

In vitro Acidification of Yeast Vacuoles and *E. coli* Membrane Vesicles

Figure 2A:
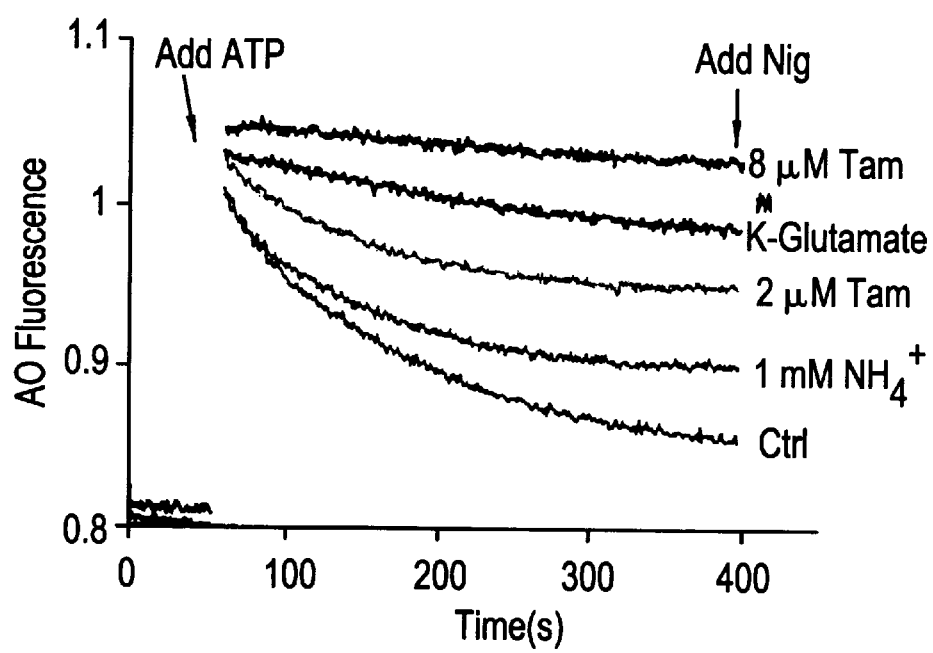
FIGS. 2A–2B show the effect of tamoxifen on acidification of yeast vacuoles.

Acidification of Yeast Vacuoles:

To test if tamoxifen inhibited acidification in yeast vacuoles, in vitro acidification of vacuoles was assayed using AO. The buffer was pre-equilibrated with either carrier (DMSO), tamoxifen (2 μM or 8 μM), ammonium chloride (1 mM), or concanomycin A (10 nM), or in K-glutamate instead of KCl buffer (FIG. 2A). ATP (1.5 mM) was added at 50 sec to initiate acidification and at 400 sec nigericin (1 μM) was added to dissipate pH gradients. As observed in mammalian microsomes, tamoxifen shows a dose dependent inhibition of acidification, with complete inhibition at 8 μM. This strongly implies that tamoxifen inhibits acidification independent of the estrogen receptor which is not found in yeast. Acidification was slightly inhibited by the weak base anmmonium chloride (1 mM). This is 1000-fold greater than the concentration of tamoxifen required to achieve similar inhibition.

Figure 2B:
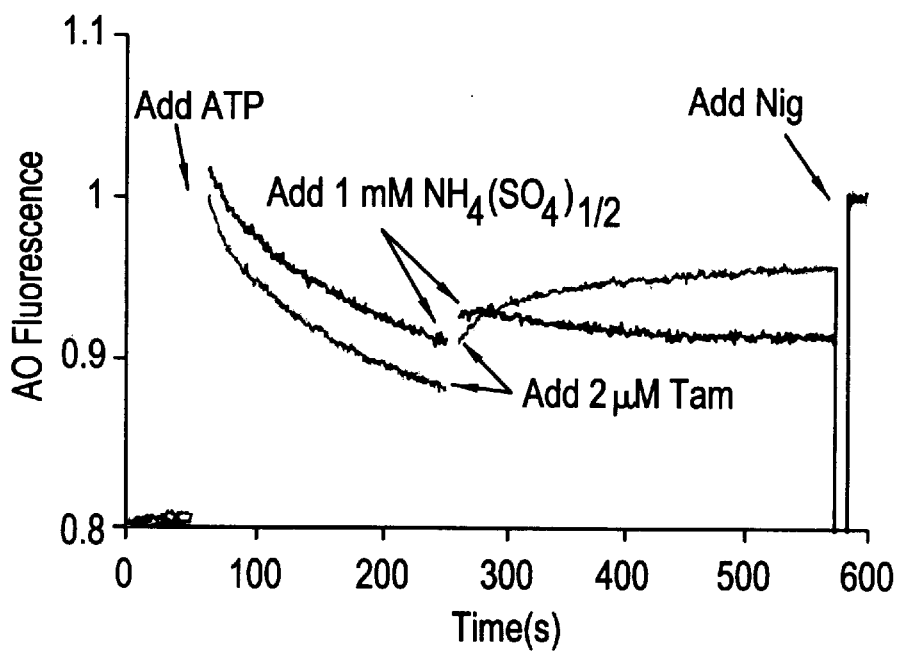

Addition of tamoxifen to pre-acidified vacuoles (at 250 sec in FIG. 2B) resulted in a rapid alkaline step followed by slower alkalinization. The step is reminiscent of a weak base which rapidly establishes equilibrium across vesicles. Thus, a comparison was made of the effects of adding tamoxifen and the weak base ammonium to pre-acidified vacuoles (FIG. 2B). Addition ammoniaum (1 mM) indeed caused a step alkalinization. However, the vacuoles slowly re-acidify after addition of ammonium but continue to alkaiinize after addition of tamoxifen.

Membrane Potential:

The fluorescent dye Oxonal V was used to monitor $V_m$. Oxonol V contains two delocalized negative charges and is highly lipophilic. In the presence of vesicles with positive $V_m$, it accumulates in the lumen and inner leaflet, resulting in fluorescence quenching [Schernan and Henry, *Biochim.Biophys.Acta*, 599:150–166 (1980)]. Unlike AO, which exhibits quenched fluorescence in the presence of acidified vesicles regardless of the number of non-acidified vesicles present, Oxonol V will report an average $V_m$ for all vesicles. This necessitates the use of pure preparations, such as the yeast vacuoles.

Figure 3B:
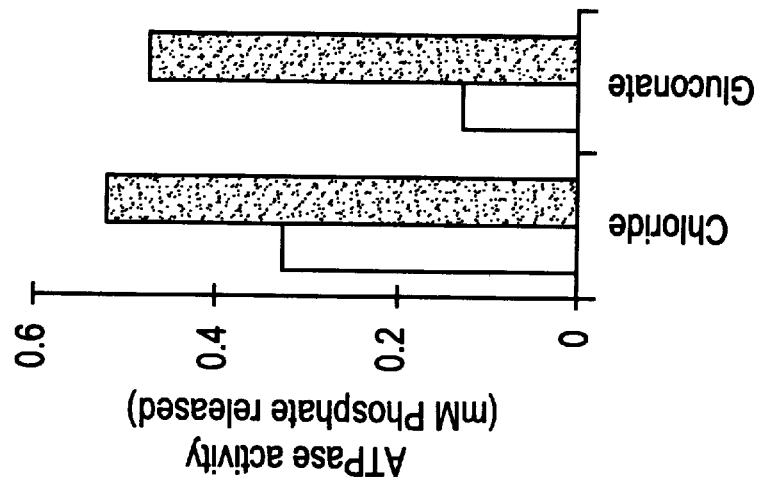
FIGS. 3A–3B shows the effect of tamoxifen on $V_m$ and vacuolar ATPase activity of yeast vacuoles.
Figure 3A:
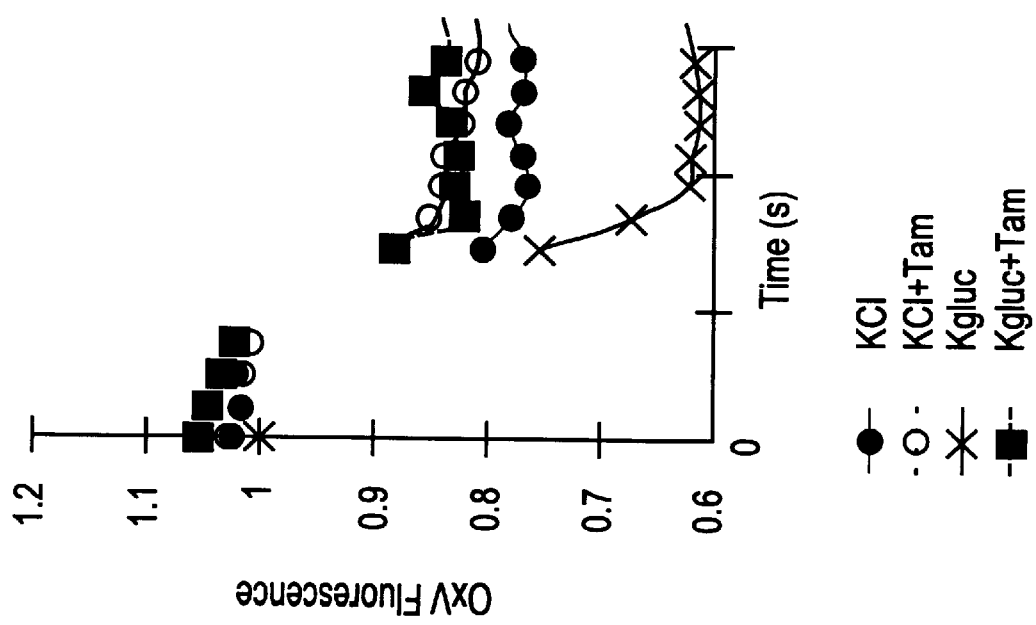

The $V_m$ was monitored in either KCl or K-gluconate buffer (FIG. 3A). At 50 sec, tamoxifen (10 μM) or carrier was added and acidification was initiated by adding ATP (2.5 mM) at 200 sec. A larger positive $V_m$ was generated in K-gluconate than in KCl which implicates a chloride permeability in dissipating the $V_m$ of the vacuoles. Tamoxifen significantly decreased the $V_m$ generated by the vATPase. This suggests that tamoxifen may increase ion permeability thus decreasing the $V_m$.

ATPase Activity:

To specifically assay the vATPase activity, the effects of tamoxifen were quantified on the bafilomycin-inhibitable ATPase activity. Replacing chloride with gluconate decreased the bafilomycin-inhibitable ATPase activity (FIG. 3B), further confirming that chloride provided the counter-ion transport to dissipate the $V_m$. Addition of tamoxifen caused an increase of ATPase activity in both conditions, with a more dramatic increase in gluconate buffer (FIG. 3B).

In summary, in yeast vacuoles tamoxifen inhibited ATP dependent acidification, decreased $V_m$, and increased bafilomycin-inhibtable ATPase activity. These results are consistent with the hypothesis that tamoxifen increases membrane permeability to protons, either through direct lipid interaction, or through proteins or modulators (see Table 1 above).

Acidification of *E. coli* Inverted Membrane Vesicles:

To test the protein and lipid specificity of acidification inhibition by tamoxifen, the effects of tamoxifen on ATP-dependent acidification in *E. coli* inverted vesicles (InV) was assayed. Unlike mammalian or yeast vesicles, InV utilize the $F_0F_1$-ATPase for acidification and are composed of different types of lipids, including an abundance of cardiolipin and a lack of sterols.

Figure 4:
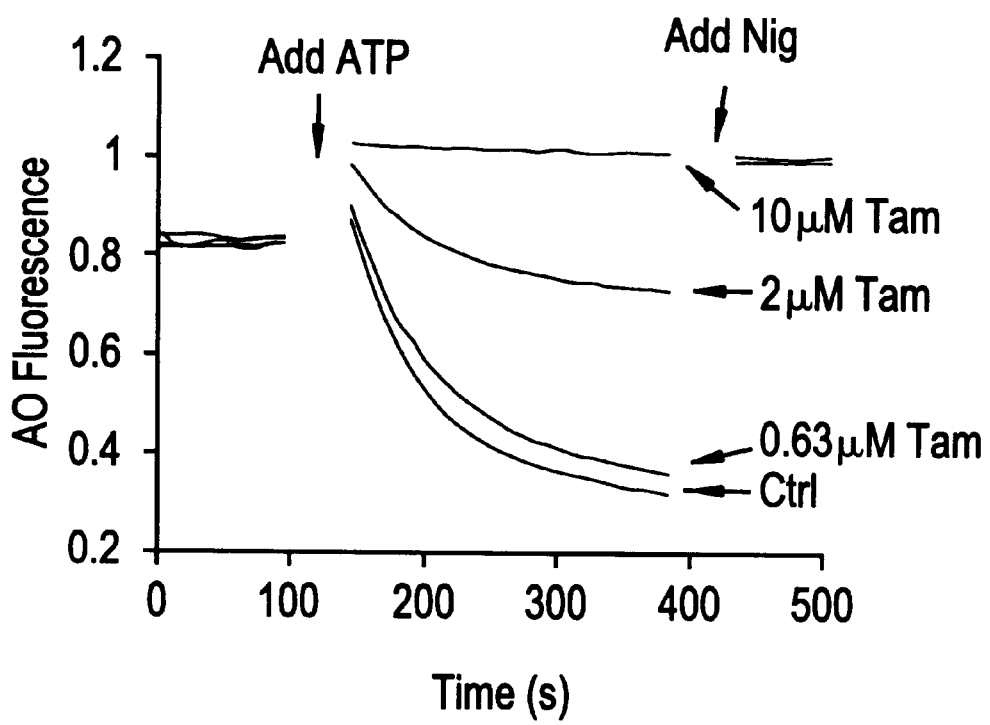
FIG. 4 shows the effect of tamoxifen on acidification of *E. coli* inverted membrane vesicles. InV were suspended in KCl buffer with 6 μM AO in the presence (0.63 μM, 2 μM 10 μM) or absence of tamoxifen. ATP (1.5 mM) and nigericin (1 μM) were added at 100 sec and 400 sec. Consistent with the results of the two mammalian microsomes examined (see FIGS. 1 and 2) and yeast vacuoles (see FIG. 3), tamoxifen inhibited ATP-dependent acidification.

As shown in FIG. 4, the presence of tamoxifen inhibited acidification in InV with a similar dose dependence as observed in mammalian and yeast vesicles (see FIGS. 1A, 2A). Similarly, addition of tamoxifen to *E. coli* vesicles pre-acidified with ATP resulted in similar rates of alkalinization as mammalian and yeast vesicles (FIGS. 1A, 2A). These results indicate that tamoxifen can dissipate pH gradients across a diverse spectrum of native biological membranes.

Liposomes pH Gradients:

The effect of tamoxifen on pH gradients was tested in pure lipid vesicles. This system was used both because the effects of tamoxifen on acidification were observed in diverse biological membranes and because the results on the ATPase activity was consistent with tamoxifen affecting membrane permeability to protons.

Liposomes were loaded with pyranine, a hydrophilic, non-permeable fluorescent pH indicator to assay proton permeability. The log of the ratio of the fluorescence emission of pyranine when excited at $\lambda_{ex}$=405 nm and $\lambda_{ex}$=455 nm is linearly dependent on the pH (FIG. 5)[Kano and Fendler, *Biochim.Biophys.Acta* 509:289–299 (1978); Clement. and Gould, *Biochemistry* 20:1534–1538 (1981)]. Two steps were taken to ensure that only $pH_L$ was measured and to permit the discrimination between dissipation of pH gradient and the lysis or dye leakage from liposomes. First, greater than 95% of external pyranine was removed by gel filtration. Second, the membrane impermeable quencher p-xylene-bis-pyridinium bromide (DPX) was added to the external solution [Ladokhin et al., *Biophys.J.* 69:1964–1971 (1995)] which effectively quenched all remaining non-lumenal pyranine fluorescence.

To mimic the acidified lumen of organelles, liposomes were made with the $pH_L$ buffered at 6.2. The $pH_L$ was monitored while the external pH (at 50 sec) was shifted to 7.3 (FIG. 6A) in the presence tamoxifen (0, 0.5 μM or 2 μM).

Nigericin (1 μM) was added at 700 sec to dissipate pH gradients. In the absence of tamoxifen, the $pH_L$ increased less than 0.2 pH unit over the 10 minute span. In the presence of tamoxifen, after a shift of external pH, there was a rapid step increase in $pH_L$. The proton permeability of liposomes after the step increase is difficult to compare with the control, since the pH gradient has decreased. Tamoxifen did not induce detectable leakage of pyranine and, in solution, tamoxifen does not affect pyranine fluorescence.

Figure 6A:
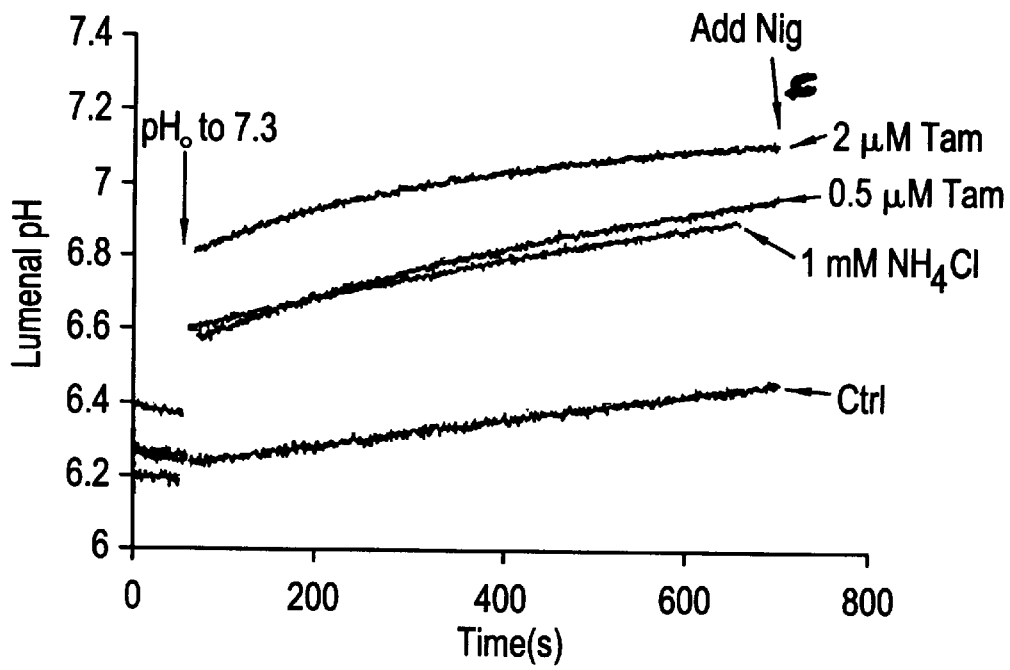
FIGS. 6A–6B show the rate of pH equilibration of pH=6.3 liposomes in pH=7.3 bath. Pyranine loaded liposomes with $pH_{in}$=6.3 was diluted into KCl buffer of same pH and 10 mM DPX and one of the follow compounds: carrier, tamoxifen (0.5 μM, 2 μM), NH$_4$Cl (1 mM), FCCP (1 μM) or valinomycin (1 μM). At 20 sec, 5 mM K-glycylglycine pH 8.4 was added to raise $pH_{out}$=7.3. At 700 sec, 1 μM nigericin was added to equilibrate the pH.
Figure 6B:
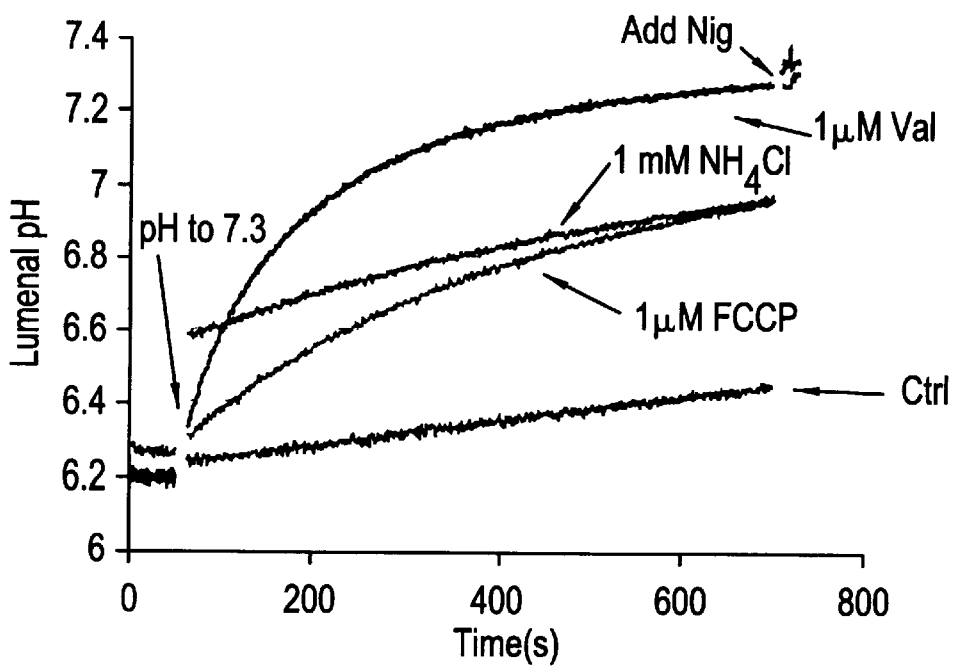

The effects of tamoxifen on $pH_L$ were contrasted with the effects of other pH-perturbants with known mechanisms of action, specifically a protonophore (FCCP), a potassium ionophore (valinomycin), and a weak base ($NH_4Cl$) (FIG. 6B). FCCP at saturating concentrations only slowly dissipated the pH gradient. This is because FCCP allows free movement of only protons. Thus proton efflux down its gradient generates a $V_m$ preventing further proton movement. The presence of valinomycin, a $K^+$-selective ionophore which would dissipate $V_m$, caused a faster dissipation of the pH gradient than FCCP (FIG. 6C). Here, protons can efflux down the concentration gradient without generation of $V_m$. Thus, these liposomes were more permeable to protons than potassium. As expected, the combination of FCCP and valinomycin immediately dissipated the pH gradient coiparable with the effects of nigericin. The weak base $NH_4Cl$ caused a step alkaline shift, followed by a slow alkaline drift. Here, the alkaline shift is caused by the selective diffusion of the basic $NH_3$ into the vesicles while the acidic $NH_4^+$ is impermeable. Of the three agents tested, the effect of micromolar concentrations of tamoxifen is most similar to the effect observed at millimolar concentrations of $NH_4Cl$: the step alkalinization upon changing the external pH was similar, but the subsequent dissipation of pH was faster with 0.5 μM tamoxifen (FIG. 6A).

Figure 7A:
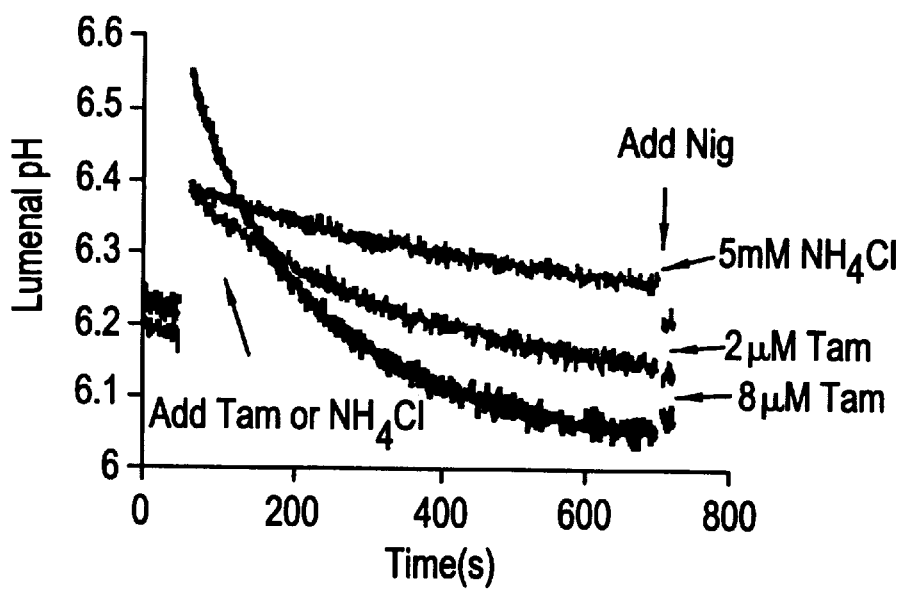
FIGS. 7A–7B show the basis for weak base effect of tamoxifen.

The potential contribution of a weak-base effect in the mechanism of tamoxifen action was further explored using liposomes in the absence of a pre-existing pH gradient. The $pH_L$ was monitored and tamoxifen (2 μM, 8 μM) or $NH_4Cl$ (5 mM) was added at 50 seconds. At 700 seconds, nigericin was added to dissipate the pH gradient. As expected, upon addition of the weak base $NH_4Cl$, the non-protonated species ($NH_3$) rapidly diffused into the liposomes, where it was protonated causing alkalinization of the lumen (FIG. 7A). The pH gradient slowly dissipated by either leakage of $H^+$ or $NH_4^+$. Similarly, addition of tamoxifen caused alkalinization of liposomes, followed by more rapid pH equilibration (FIG. 7A). This suggests that like ammonia, tamoxifen-free-base rapidly enters liposomes, causing a step alkaline shift in the lumen while the protonated tamoxifen is less permeable.

The observation that tamoxifen exerted similar effects to $NH_4Cl$ at three orders of magnitude lower concentration suggests that it may be highly concentrated within liposomes. The extent of lipid partitioning of tamoxifen was examined by measuring the partitioning coefficient of tamoxifen between octanol and aqueous buffer.

Figure 7B:
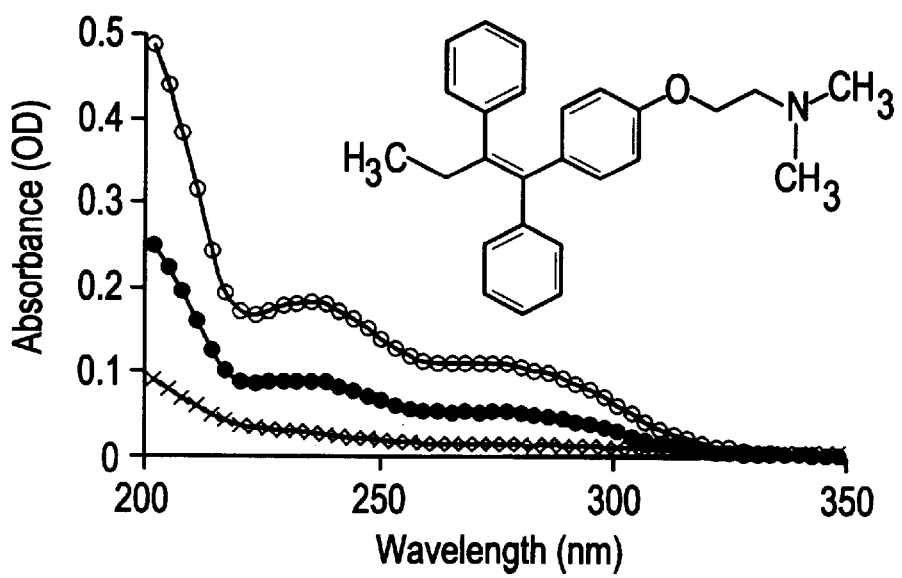

Tamoxifen in aqueous solution was equilibrated with either 1:1000 or 1:100 volume of octanol and the concentration of tamoxifen left in the aqueous phase was measured by absorbance (FIG. 7B). Notice that 1:1000 volume octanol was able to extract approximately 50% of tamoxifen in aqueous solution, suggesting that tamoxifen partitions three orders of magnitude greater into the lipid phase. Octanol partitioning was repeated with the aqueous phase buffered pH 1 and pH 13 to examine possible differences in partitioning between the charged and neutral forms of tamoxifen respectively. The same result was obtained at both pH values. This is consistent with the difference in concentrations of $NH_4Cl$ and tamoxifen required for the same quantitative effect. It may also contribute to the observation that pyranine reports a lower $pH_L$ in the presence of tamoxifen even after addition of nigericin (FIG. 7A). Tamoxifen could effectively give the liposomes a positive surface charge, which has been shown to effect pyranine fluorescence [Kano and Fendler, Biochim.Biophys.Acta 509:289–299 (1978)].

Figure 8A:
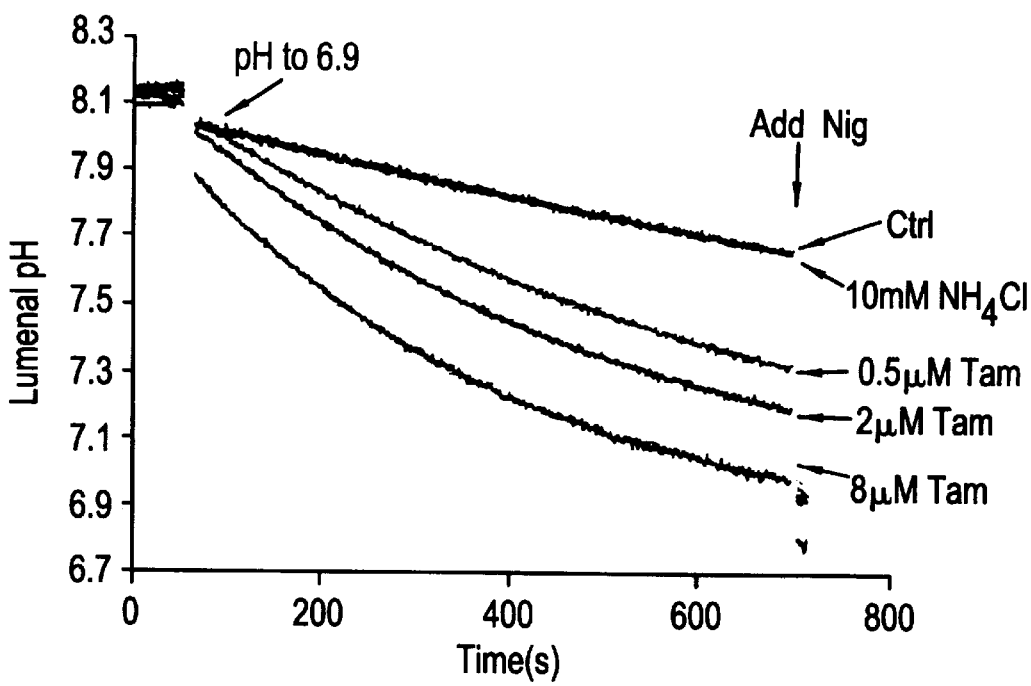
FIGS. 8A–8B show the rate of pH equilibration of pH=8.1 liposomes in pH=6.9 bath. Pyranine loaded liposomes with $pH_{in}$=8.1 was diluted into KCl buffer of same pH and 10 mM DPX and one of the follow compounds: carrier, tamoxifen (0.5 μM, 2 μM, 8 μM), NH$_4$Cl (10 mM), FCCP (1 μM), valinomycin (1 μM) or both tamoxifen (8 μM) and valinomycin (1 μM). At 50 sec, 5 mM K-MES was added to lower $pH_{out}$ to 6.9.

In both yeast vacuoles (FIG. 2B) and liposomes (FIG. 7A), addition of tamoxifen or ammonium caused similar pH jumps, but tamoxifen subsequently caused a more rapid equilibration of pH. This suggests that other mechanism(s) may contribute in addition to the weak base effect. In liposomes with an acidic lumen, the initial weak-base alkaline jump is too large to allow an assessment of the rate of subsequent pH dissipation. Therefore, the effects of tamoxifen and a weak base were tested on liposomes with an alkaline interior pH of 8.1. The $pH_L$ was monitored after shifting the external pH to 6.9 by the addition of 4 mM MES pH 5 at 50 sec (FIG. 8A). The pH gradient was dissipated more quickly with increasing concentrations of tamoxifen. In contrast, the effect of $NH_4Cl$ (5 mM) was indistinguishable from the control. Thus, the dissipation of pH by tamoxifen cannot be solely explained as a weak-base effect.

Figure 8B:
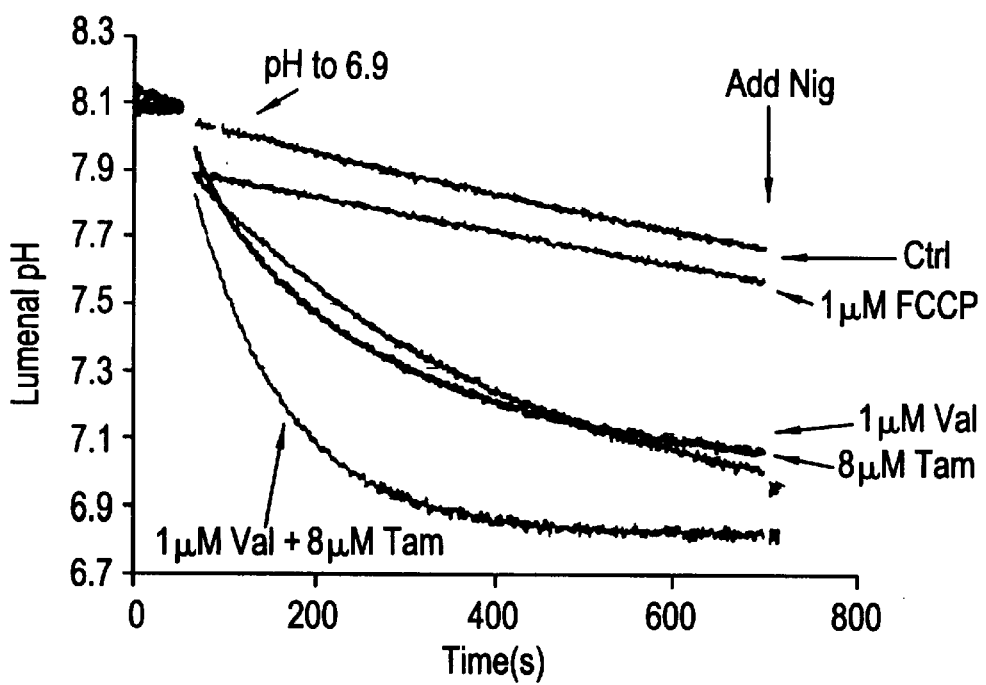

To explore potential ionophoretic mechanisms, tamoxifen was compared with FCCP and valinomycin (FIG. 8B). Addition of FCCP did not substantially increase the rate by which the pH gradient was dissipated, presumably because proton leakage is limited by the $V_m$. This is substantiated by the observation that valinomycin caused a greater dissipation of pH gradient than FCCP.

The observation that tamoxifen diminished the pH gradient faster than saturating concentration of FCCP (FIG. 8B) implies that tamoxifen cannot be a pure protonophore. Any pure protonophore will, like FCCP, allow free proton movement but be limited by $V_m$. Importantly, when both tamoxifen and valinomycin were included, the effect was additive and not synergistic. This implies that tamoxifen mediated proton movement is electroneutral. If tamoxifen mediated an electrogenic process (e.g., pure protonophore), the dissipation of the $V_m$ by valinomycin would dramatically increase the effect of tamoxifen. For example, the presence of valinomycin allows FCCP to immediately dissipate any pH gradient.

Chloride Permeability:

If tamoxifen mediates bidirectional electroneutral transport of protons, then a second ion must be co-transported. Chloride could be this ion. Therefore, the effect of tamoxifen on the influx of chloride into liposomes was examined. Lucigenin, a fluorescent dye that is collisionally quenched by chloride was employed [Biwersi et al., Proc.Natl.Acad.Sci.USA 93:12484–12489 (1996)]. Liposomes were loaded with $KNO_3$ buffer and lucigenin. The lumenal chloride concentration can be accurately calibrated by the fluorescence.

Figure 9A:
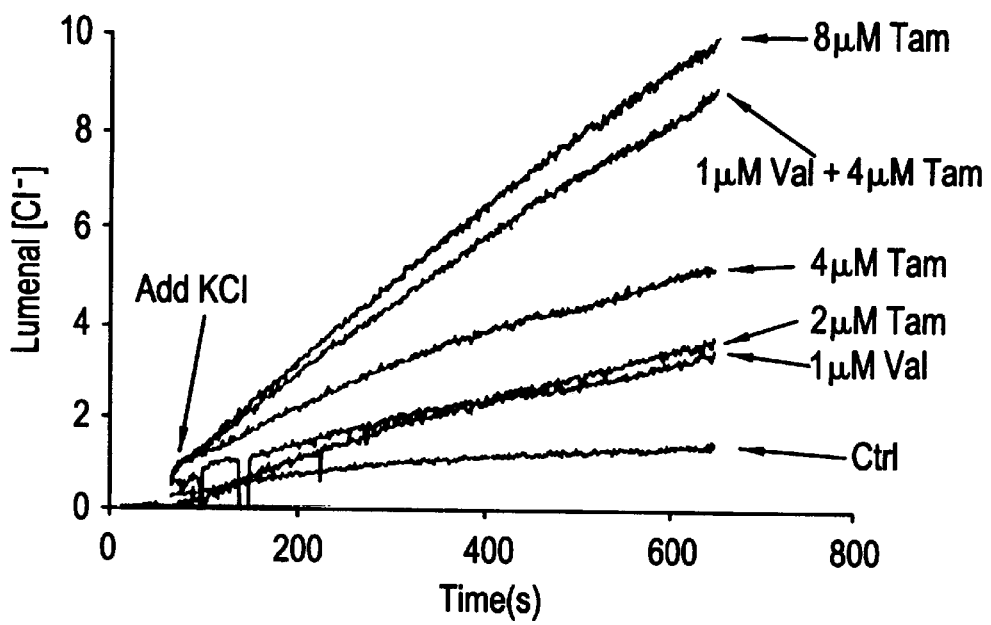
FIGS. 9A–9C show the effect of chloride on tamoxifen mediated proton permeability.

Lumenal chloride concentration in the liposomes was monitored after addition of 50 mM KCl to the external solution (FIG. 9A). Tamoxifen caused a dose dependent increase in the rate of chloride influx. Since chloride is more membrane permeable than potassium, unidirectional chloride movement is also expected to be limited by $V_m$ [Paula et al., Biophys.J. 70:339–348 (1996)]. Indeed, the presence of valinomycin increased the rate of chloride equilibration. To test if tamoxifen was affecting chloride permeability solely by dissipation of the $V_m$, tamoxifen was added to liposomes in the presence of a concentration of valinomycin (1 $\mu$M) that completely dissipates the $V_m$ (FIG. 9A). The addition of 4 $\mu$M tamoxifen increased the rate of chloride influx observed in the presence of valinomcyin. This indicates that tamoxifen must be having an effect on chloride permeability independent of any effects on $V_m$. In addition, the fact that the effects tamoxifen and valinomycin were additive on chloride permeability also indicates that the chloride transport is electroneutral.

Figure 9B:
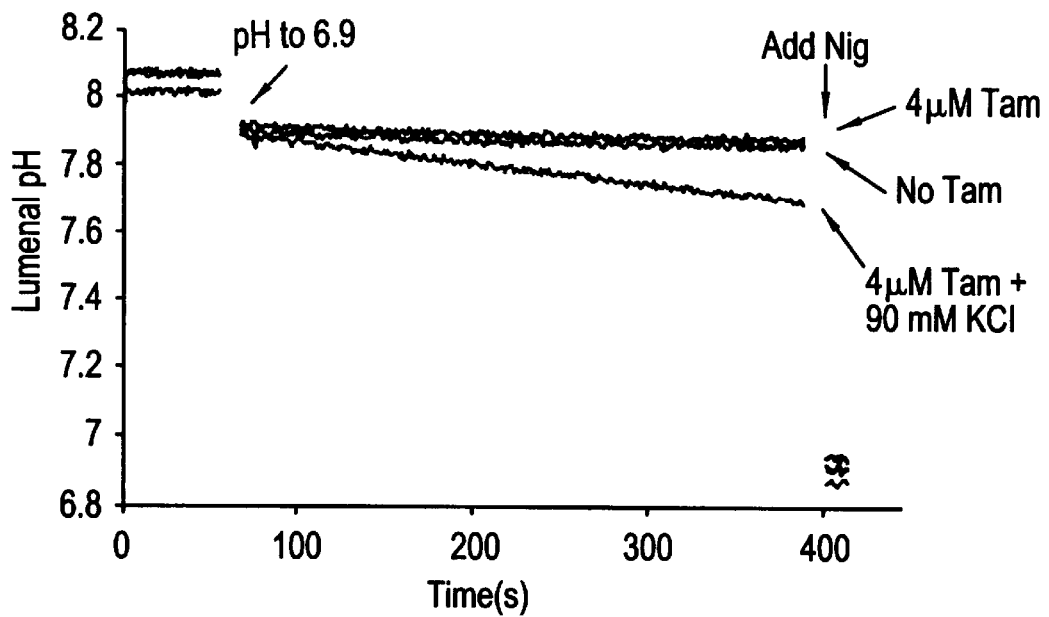

Since tamoxifen seems to increase both proton and chloride permeability, it was determined as whether tamoxifen mediates their coupled transport (ie., the crossing of HCl, but not $H^+$ or $Cl^-$ independently). If tamoxifen mediates coupled transport, then chloride would be necessary for tamoxifen mediated proton permeability. Thus, the effect of tamoxifen on pH in the absence of chloride was assessed. Pyranine loaded liposomes with a lumenal pH of 8.1 were resuspended in 300 mM K-glutamate and then the external pH was shifted to 6.9 (FIG. 9B). Tamoxifen had no effect on the dissipation of pH. Inclusion of 90 mM KCl resulted in more rapid pH equilibration (FIG. 9B). In the absence of tamoxifen, addition of 90 mM KCl had no effect. This indicates that external chloride is required for tamoxifen-mediated acidification of the lumen of the liposomes.

Figure 9C:
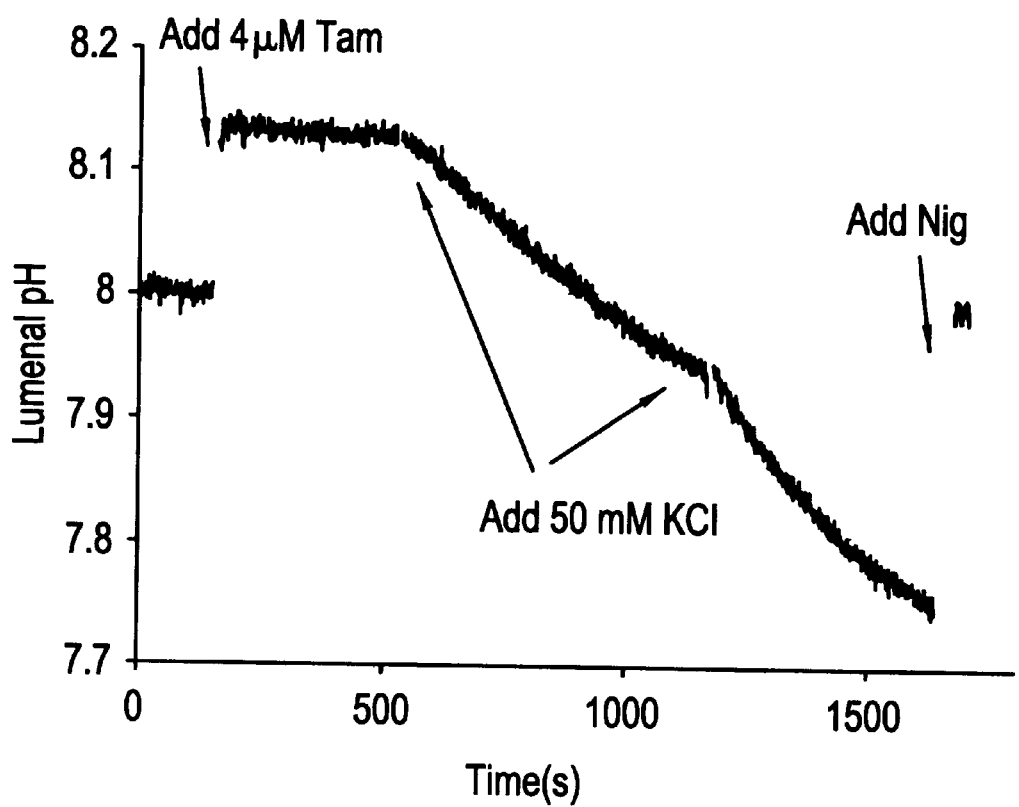

To further test if tamoxifen is acting as a coupled $Cl^-/H^+$ co-transporter, the effect of chloride gradients on lumenal pH were analyzed in the presence of tamoxifen. In liposomes with no lumenal chloride, addition of KCl to the external solution results in a large chloride gradient. If tamoxifen were acting as a coupled $Cl^-/H^+$ co-transporter, the chloride influx should mediate proton influx and lumenal acidification. Liposomes were equilibrated to pH 8.0 both inside and out (FIG. 9C). Upon addition of tamoxifen there was a rapid step alkaline shift of the lumen of the liposomes due to a weak-base effect. Moreover, upon each successive addition of 50 mM KCl there was an acidic shift of the lumenal pH. This indicates that tamoxifen coupled HCl transport mediates the rapid re-equilibration and explains why re-equilibration is faster when tamoxifen was added compared to $NH_4Cl$.

Discussion

Tamoxifen inhibits ATP dependent acidification in intact cells [Altan et al., Proc Natl Acad Sci U.S.A. 96:4432–4437 (1999) ], mammalian organelles (FIG. 1), yeast vacuoles (FIG. 2), and InV (FIG. 4). Tamoxifen also dissipates pH gradients in liposomes (FIGS. 6–9). The tamoxifen-dependent dissipation of the pH gradient is independent of all proteins including the estrogen receptor.

Figure 10:
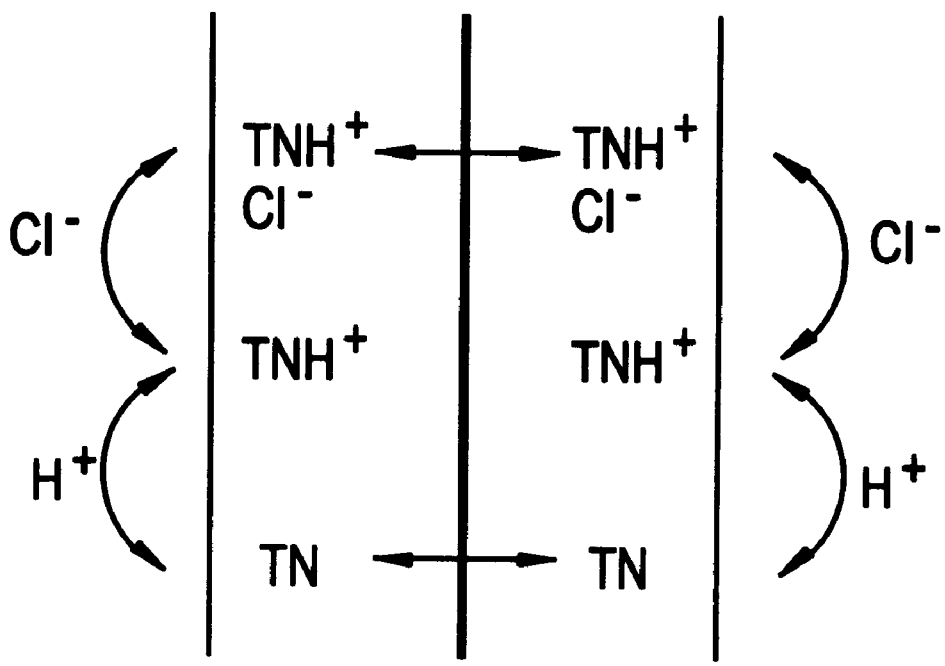
FIG. 10 shows a model for tamoxifen mediated proton permeability. Tamoxifen is concentrated within the lipid bilayer and exists as a charged protonated form (TNH⁺) or uncharged form (TN). The uncharged form is readily membrane permeable and the charged form is impermeable. This accounts for the weak base activity of tamoxifen. In addition, TNH⁺ can permeate the membrane when carrying a chloride ion, accounting for the chloride dependent electroneutral proton permeability.

The present results indicate that tamoxifen affects transmembrane pH through at least two independent mechanisms: as a weak base and as a mediator of coupled transport of proton/hydroxide and chloride. For vesicles with an acidified lumen, tamoxifen causes a rapid alkaline shift of the $pH_L$ which is most likely a weak base effect (FIG. 10). Tamoxifen is most likely highly concentrated within the leaflets of membranes. Since tamoxifen is a weak base its neutral form can readily flip between inner and outer leaflets while the charged form flips much less readily. Therefore, it will accumulate within the inner leaflet of acidic organelles, causing a step alkalinization.

However, a weak-base effect is not sufficient to account for many of the effects of tamoxifen on transmembrane pH. Tamoxifen, but not ammonium, can increase pH equilibration rate when the lumen of the liposome is alkaline relative to the bath Further, chloride is necessary for tamoxifen mediated proton permeability and a chloride gradient can generate a pH gradient in the presence of tamoxifen. One mechanism for this process is that the permeability of the protonated form of tamoxifen increases when it is conjugated to chloride (FIG. 10).

The fact that tamoxifen inhibits acidification in so many model systems indicates that tamoxifen should affect organellar pH in many different cell types. This is consistent with the observations that tamoxifen administration has numerous physiological sequelae that are not restricted to cells expressing the estrogen-receptor. Of particular significance is the observation that blocking organelle acidification through other means is sufficient to reproduce many of the effects of tamoxifen. Tamoxifen blocks bone resorption which is also blocked by antagonists of the vATPase [Sundquist et al., *Biochemical & Biophysical Research Communications* 168:309–313 (1990)]. In drug-resistant tumor cells tamoxifen redistributes chemotherapeutics from the organelles to the cytoplasm [Altan et al., *Proc Natl Acad Sci U.S.A.* 96:4432–4437 (1999); Hurwitz et al., *Blood* 89:3745–3754 (1997); Schindler et al., *Biochemistry* 35:2811–2817 (1996)] and increases the sensitivity of the cells to chemotherapeutics [Schindler et al., *Biochemistry* 35:2811–2817 (1996)]. These effects can be reproduced solely by mimicking the effects of tamoxifen on organellar acidification either with the use of protonophores, weak bases, or inhibitors of the vATPase [Altan et al., *J.Exp.Med.* 187:1583–1598 (1998); Hurwitz et al., *Blood* 89:3745–3754 (1997); Schindler et al., *Biochemistry* 35:2811–2817 (1996)]. Tamoxifen decreases the rate of vesicle sorting and secretion which is also seen when organelle acidification is blocked with protonophores [Tartakoff, *Cell* 32:1026–1028 (1983)]. Many secreted proteins are activated by a pH-dependent proteolytic step in the Golgi. Thus, the reduced activity of many secreted proteins observed with tamoxifen treatment may also be the consequence of a tamoxifen block of organelle acidification.

Consistent with previous reports [Wiseman, *Trends in Pharmacological Sciences* 15:83–89 (1994)], tamoxifen was observed to accumulate in the lipid phase (1000:1) over the aqueous environment. Further, the present results indicate that membrane-bound tamoxifen is in equilibrium between a neutral and protonated form. Thus, tamoxifen would be expected to significantly perturb many properties of cellular membranes, including increased surface charge, and altered membrane tension. These effects have been reported for lipophilic weak base anesthetics [Gruner and Shyamsunder, *Ann.N.Y.Acad.Sci.* 625:685–697 (1991); Seelig et al., *Biochim.Biophys.Acta* 939:267–276 (1988); Sato et al., *Journal of Experimental Medicine* 123:185–190 (1977)]. The altered membrane properties could shift the voltage dependence of many ion channels. Indeed, tamoxifen has been reported to shift the activity of many ion channels [Zhang et al., *Journal of Clinical Investigation* 94:1690–1697 (1994); Ehring et al., *J.Gen.Physiol.* 104:1129–1161(1994); Greenberg et al., *Cancer Res.* 47: 70–74 (1987); Song et al., *Journal of Pharmacology & Experimental Therapeutics* 277: 1444–1453 (1996); Williams et al., *J.Biol.Chem.* 271: 12488–12495 (1996); Turner et al., *Endocrinology* 122: 1146–1150 (1988)]. Details studies on the model channel, gramicidin, have shown that membrane tension [Goulian et al., *Biophys.J.* 74:328–337 (1998)] and surface charge [Rostovtseva et al., *Biophys.J.* 75:1783–1792 (1998)] are critical determinants of channel activity.

These results demonstrate that many of the effects of tamoxifen on cells can be attributed to either membrane active effects on organelle acidification or surface charge. Each of these effects are independent of the estrogen receptor. This suggests that it should be possible to screen for other estrogen-receptor antagonists that do not also affect organellar acidification and therefore may not share the same physiological effects as tamoxifen.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all base sizes or amino acid sizes, and all molecular weight or molecular mass values, given for nucleic acids or polypeptides are approximate, and are provided for description.

Various publications are cited herein, the disclosures of which are incorporated by reference in their entireties.

What is claimed is:

1. A method of selecting for an agent which binds to the estrogen receptor but which dissipates a transmembrane pH gradient to a lesser extent than does tamoxifen, wherein the method comprises:

(a) choosing an agent which binds to the estrogen receptor, (b) choosing a vesicle and conditions wherein the pH inside the vesicle differs from the pH outside the vesicle, whereby a transmembrane pH gradient is formed, (c) employing conditions under which tamoxifen dissipates the transmembrane pH gradient in the vesicle of step (b), and, in the absence of tamoxifen, contacting the agent of step (a) with the vesicle of step (b), (d) measuring any change in the magnitude of the transmembrane pH gradient of the vesicle when contacted with the agent, and comparing the change measured to that seen when the vesicle is separately contacted with tamoxifen, (e) selecting for the agent when the comparison of step (d) indicates that the agent dissipates the transmembrane pH gradient to a lesser extent than does tamoxifen.

2. The method of claim 1 wherein the agent does not measurably dissipate the transmembrane pH gradient.

3. The method of claim 1 wherein the change in the magnitude of the transmembrane pH gradient is measured with a fluorescent probe.

4. The method of claim 3 wherein the fluorescent probe is acridine orange.

5. The method of claim 1 wherein the vesicle is selected from the group consisting of a cell, a mammalian organelle, a yeast vacuole, an inverted bacterial membrane vesicle, and a liposome.

6. The method of claim 5 wherein the vesicle is a mammalian organelle.

7. The method of claim 6 wherein the mammalian organelle is a recycling endosome and wherein the change in the magnitude of the transmembrane pH gradient is measured with a fluorescent-labeled transferrin.

8. The method of claim 5 wherein the vesicle is a liposome.

9. The method of claim 8 wherein the change in the magnitude of the transmembrane pH gradient is measured with pyranine.

10. The method of claim 1, further comprising:

(f) measuring a surface membrane charge of the vesicle before contact with either the agent or tamoxifen, (g) measuring a surface membrane charge of the vesicle after contact with either tamoxifen or the agent, and comparing the results, (h) selecting for the agent if the agent meets the conditions of step (e) and if the agent alters the surface membrane charge of the vesicle to a lesser extent than does tamoxifen.

11. A method of selecting for an agent which binds the estrogen receptor but which alters a surface membrane charge to a lesser extent than does tamoxifen, comprising:
   (a) choosing an agent which binds to the estrogen receptor,
   (b) selecting a vesicle and conditions under which tamoxifen is known to alter a surface membrane charge of the vesicle,
   (c) in the absence of tamoxifen, contacting the agent of step (a) with the vesicle under the conditions of step (b),
   (d) measuring any alteration in the surface membrane charge of the vesicle upon contact with the agent, and comparing the measured alteration to that seen when the vesicle is separately contacted with tamoxifen,
   (e) selecting an agent when the alteration in the surface membrane charge in the presence of the agent is less than the alteration in the presence of tamoxifen.

12. The method of claim 11 wherein the agent does not measurably alter the surface membrane charge.

13. The method of claim 11 wherein the vesicle is selected from the group consisting of a cell, a mammalian organelle, a yeast vacuole, an inverted bacterial membrane vesicle, and a liposome.

14. A method of selecting for an agent which is an antagonist of the estrogen receptor but which dissipates a transmembrane pH gradient to a lesser extent than does tamoxifen, wherein the method comprises:
   (a) choosing an agent which is an antagonist of the estrogen receptor,
   (b) choosing a vesicle and conditions wherein the pH inside the vesicle differs from the pH outside the vesicle, whereby a transmembrane pH gradient is formed,
   (c) employing conditions under which tamoxifen dissipates the transmembrane pH gradient in the vesicle of step (b), and in the absence of tamoxifen, contacting the agent of step (a) with the vesicle of step (b),
   (d) measuring any change in the magnitude of the transmembrane pH gradient of the vesicle when contacted with the agent, and comparing the change measured to that seen when the vesicle is separately contacted with tamoxifen,
   (e) selecting for the agent when the comparison of step (d) indicates that the agent dissipates the transmembrane pH gradient to a lesser extent than does tamoxifen.

15. The method of claim 14 wherein the agent does not measurably dissipate the transmembrane pH gradient.

16. The method of claim 14 wherein the change in the magnitude of the transmembrane pH gradient is measured with a fluorescent probe.

17. The method of claim 16 wherein the fluorescent probe is acridine orange.

18. The method of claim 14 wherein the vesicle is selected from the group consisting of a cell, a mammalian organelle, a yeast vacuole, an inverted bacterial membrane vesicle, and a liposome.

19. The method of claim 18 wherein the vesicle is a mammalian organelle.

20. The method of claim 19 wherein the mammalian organelle is a recycling endosome and wherein the change in the magnitude of the transmembrane pH gradient is measured with a fluorescent-labeled transferrin.

21. The method of claim 18 wherein the vesicle is a liposome.

22. The method of claim 21 wherein the change in the magnitude of the transmembrane pH gradient is measured with pyranine.

23. The method of claim 14, further comprising:
   (f) measuring a surface membrane charge of the vesicle before contact with either the agent or tamoxifen,
   (g) measuring a surface membrane charge of the vesicle after contact with either tamoxifen or the agent, and comparing the results,
   (h) selecting for the agent if the agent meets the conditions of step (e) and if the agent alters the surface membrane charge of the vesicle to a lesser extent than does tamoxifen.

24. A method of selecting for an agent is an antagonist of the estrogen receptor but which alters a surface membrane charge to a lesser extent than does tamoxifen, comprising:
   (a) choosing an agent which is an antagonist of the estrogen receptor,
   (b) selecting a vesicle and conditions under which tamoxifen is known to alter a surface membrane charge of the vesicle,
   (c) in the absence of tamoxifen, contacting the agent of step (a) with the vesicle under the conditions of step (b),
   (d) measuring any alteration in the surface membrane charge of the vesicle upon contact with the agent, and comparing the measured alteration to that seen when the vesicle is separately contacted with tamoxifen,
   (e) selecting an agent when the alteration in the surface membrane charge in the presence of the agent is less than the alteration in the presence of tamoxifen.

25. The method of claim 24 wherein the agent does not measurably alter the surface membrane charge.

26. The method of claim 24 wherein the vesicle is selected from the group consisting of a cell, a mammalian organelle, a yeast vacuole, an inverted bacterial membrane vesicle, and a liposome.

* * * * *

UNITED STATES PATENT AND TRADEMARK OFFICE
CERTIFICATE OF CORRECTION

PATENT NO.   : 6,204,067 B1
DATED        : March 20, 2001
INVENTOR(S)  : Sanford M. Simon, Melvin S. Schindler and Yu Chen It is certified that error appears in the above-identified patent and that said Letters Patent is hereby corrected as shown below:

<u>Column 32,</u>
Line 30, please change Claim 24 from
"24. A method of selecting for an agent is an antagonist of the estrogen receptor but which alters a surface membrane charge to a lesser extent than does tamoxifen, comprising:" to read -- 24. A method of selecting for an agent which is an antagonist of the estrogen receptor but which alters a surface membrane charge to a lesser extent than does tamoxifen, comprising: --

Signed and Sealed this

Eighteenth Day of June, 2002

*Attest:*

*Attesting Officer*

JAMES E. ROGAN
*Director of the United States Patent and Trademark Office*